US007915572B2

(12) United States Patent
Konno et al.

(10) Patent No.: US 7,915,572 B2
(45) Date of Patent: Mar. 29, 2011

(54) IMAGING OPTICAL SYSTEM AND ENDOSCOPE PROVIDED WITH IMAGING OPTICAL SYSTEM

(75) Inventors: Mitsujiro Konno, Hino (JP); Tatsuya Orihara, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 120 days.

(21) Appl. No.: 12/499,783

(22) Filed: Jul. 8, 2009

(65) Prior Publication Data
US 2009/0273666 A1 Nov. 5, 2009

Related U.S. Application Data

(62) Division of application No. 11/941,502, filed on Nov. 16, 2007, now Pat. No. 7,576,310, which is a division of application No. 11/401,358, filed on Apr. 11, 2006, now Pat. No. 7,317,180.

(30) Foreign Application Priority Data

Apr. 27, 2005 (JP) ................................. 2005-129191

(51) Int. Cl.
*H01L 27/00* (2006.01)
*H01J 3/14* (2006.01)
(52) U.S. Cl. ..................................... 250/208.1; 250/216
(58) Field of Classification Search ............... 250/208.1, 250/216; 359/708, 718, 719; 600/101, 103, 600/117, 118, 160, 167, 176; 348/45, 65, 68; 356/241.1
See application file for complete search history.

(56) References Cited

U.S. PATENT DOCUMENTS

| 5,543,970 | A  | * | 8/1996 | Hata et al. ................. 359/690 |
| 5,576,882 | A  | * | 11/1996 | Kanamori ................. 359/434 |
| 5,598,205 | A  | * | 1/1997 | Nishioka ................... 348/65 |
| 7,331,693 | B2 | * | 2/2008 | Fujisaki .................... 362/326 |
| 7,345,829 | B2 | * | 3/2008 | Terashima et al. ......... 359/719 |
| 2003/0002174 | A1 | * | 1/2003 | Dou ........................ 359/719 |
| 2003/0171648 | A1 |   | 9/2003 | Yokoi et al. |

* cited by examiner

*Primary Examiner* — Que T Le
*Assistant Examiner* — Pascal M Bui-Pho
(74) *Attorney, Agent, or Firm* — Arnold International; Bruce Y. Arnold

(57) ABSTRACT

An imaging optical system includes a spherical or nearly spherical viewing port, an objective lens that includes an aspheric surface and is formed as a single lens element, and a solid-state image sensor that receives an image formed by the imaging optical system. Specified conditions are satisfied by the imaging optical system and the objective lens so that an in-focus image having low distortion, sufficient contrast, and formed by light rays of restricted angles of incidence is formed even for an object in contact with the viewing port. The specified conditions relate to features of the imaging optical system such as focal length and f-number of the imaging optical system, astigmatism and distortion of the imaging optical system, and pixel pitch of the solid-state image sensor. An endoscope that includes the imaging optical system is also disclosed.

5 Claims, 35 Drawing Sheets

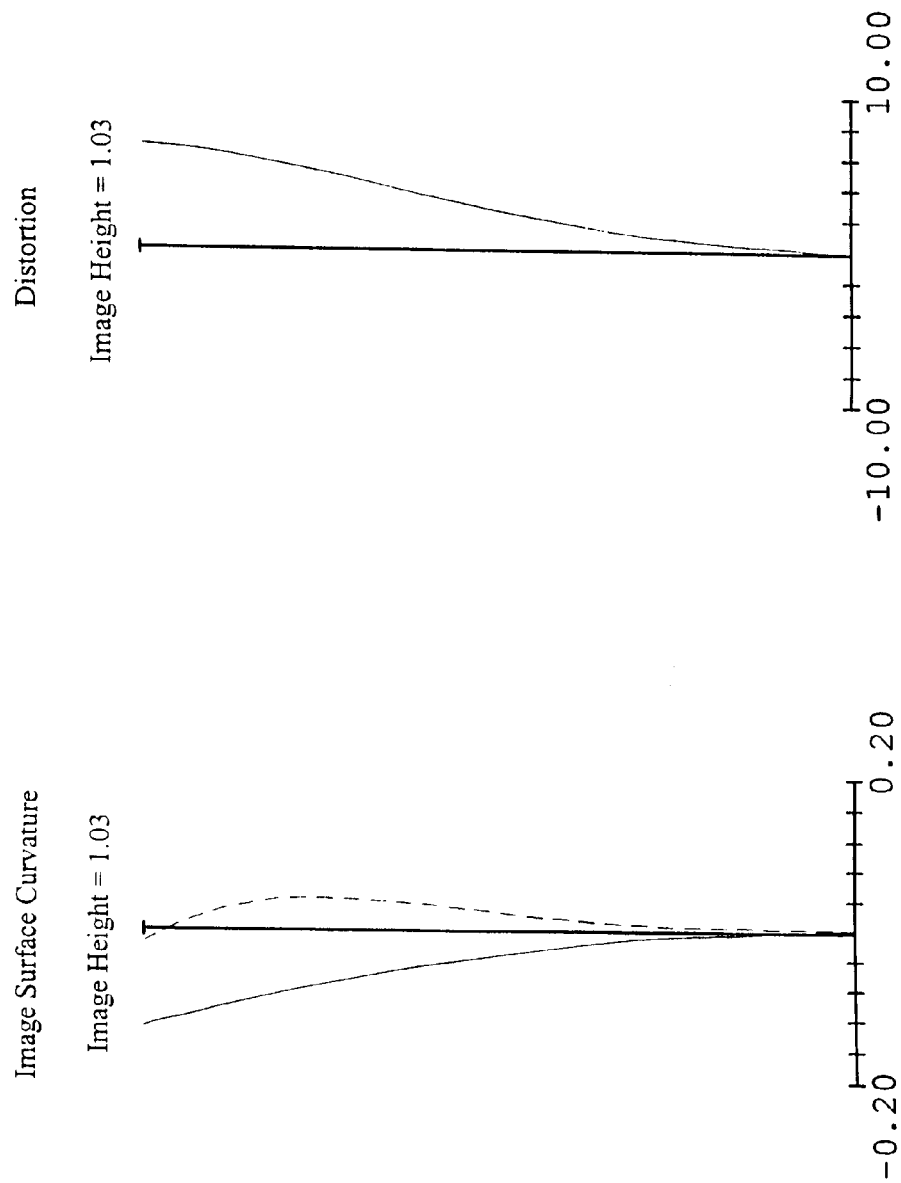

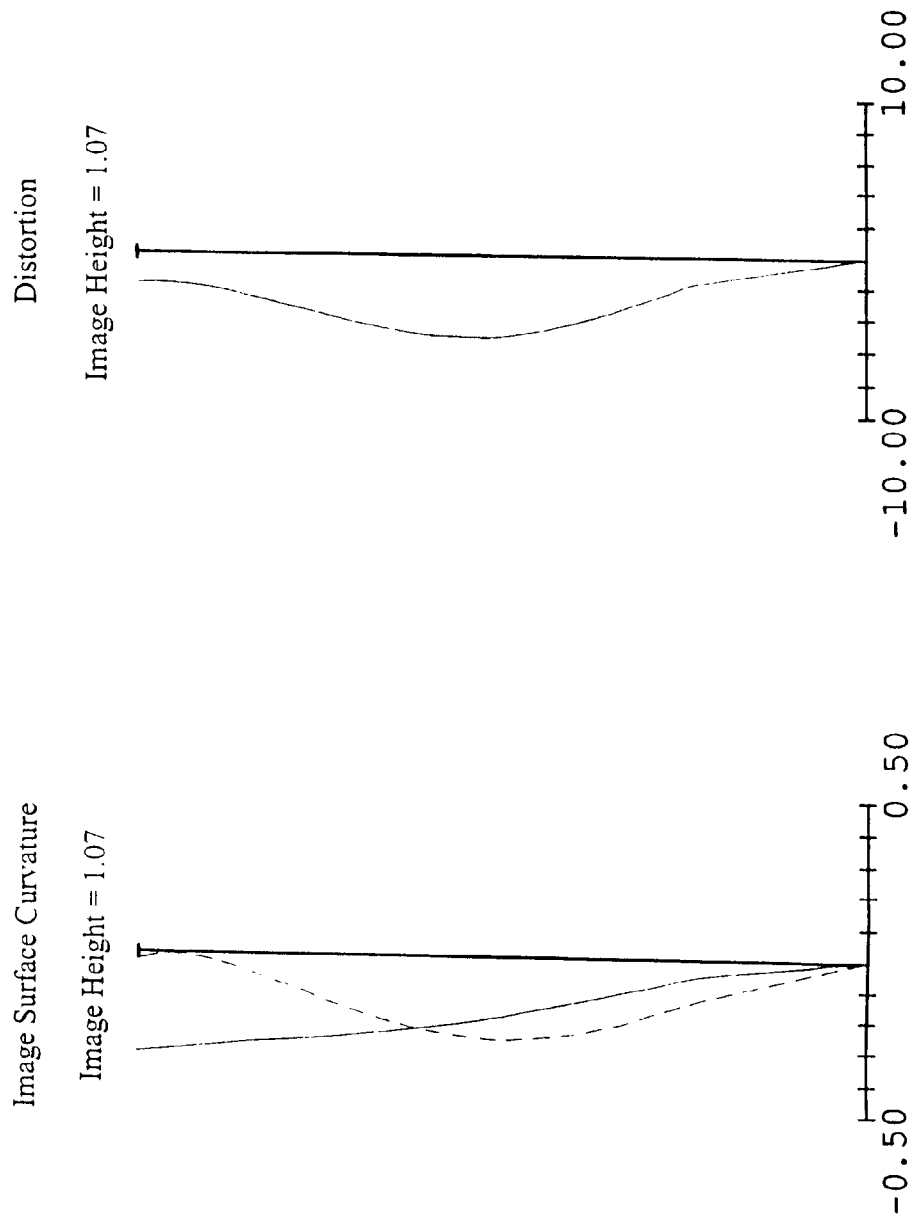

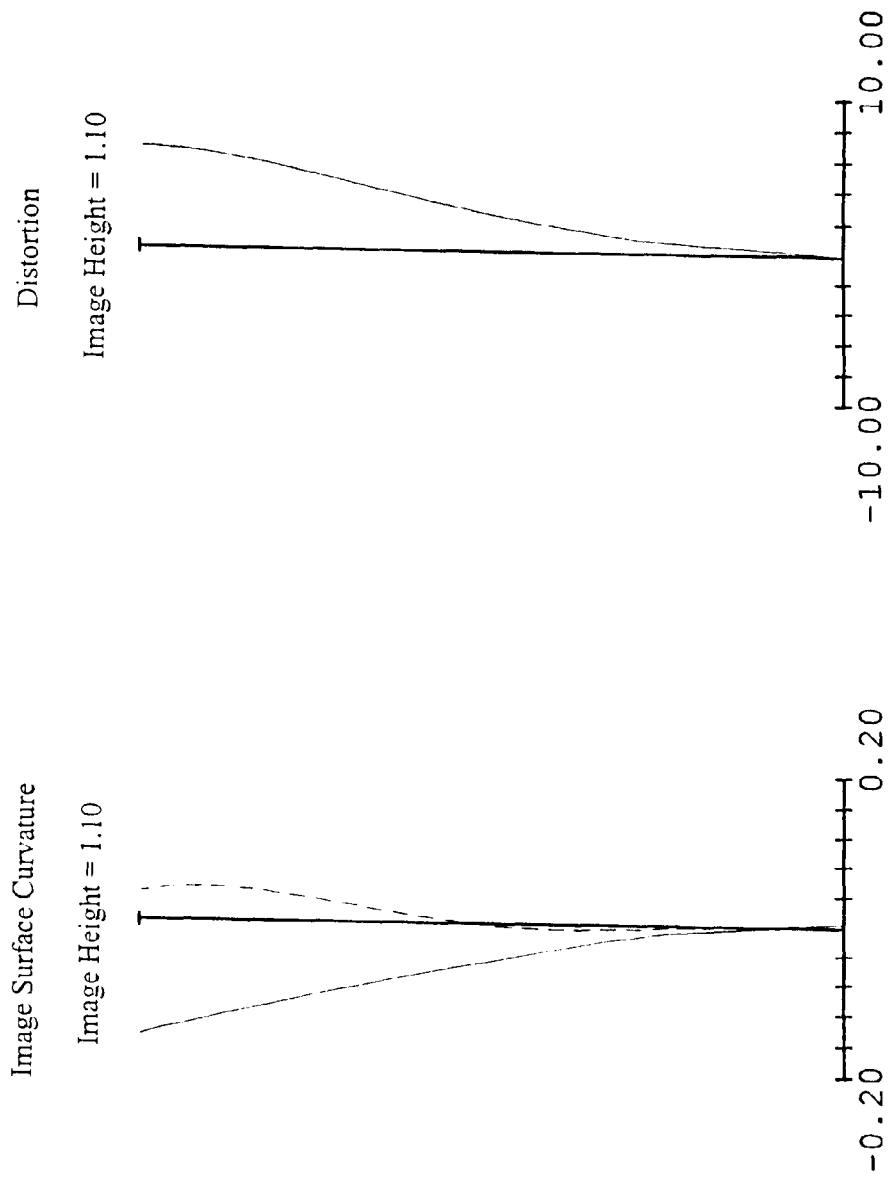

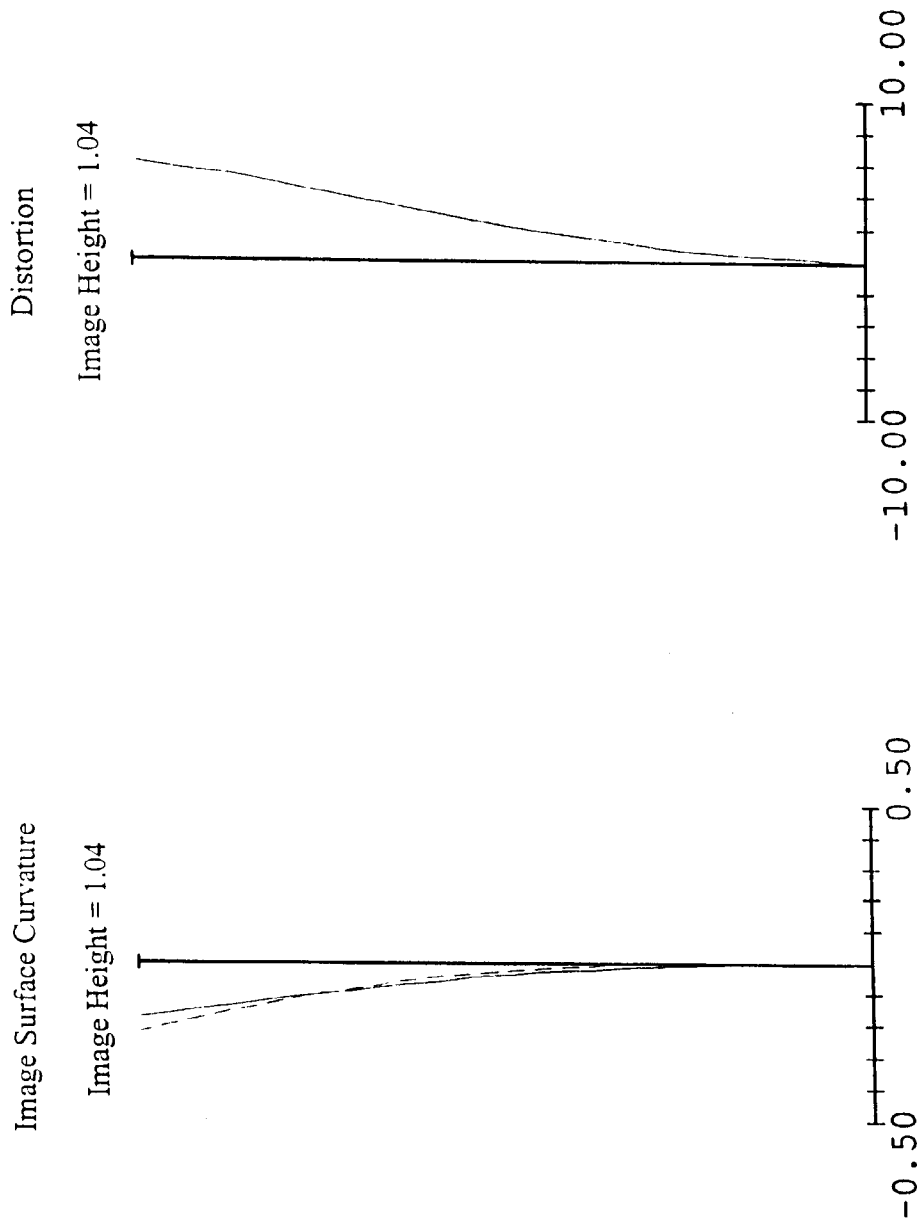

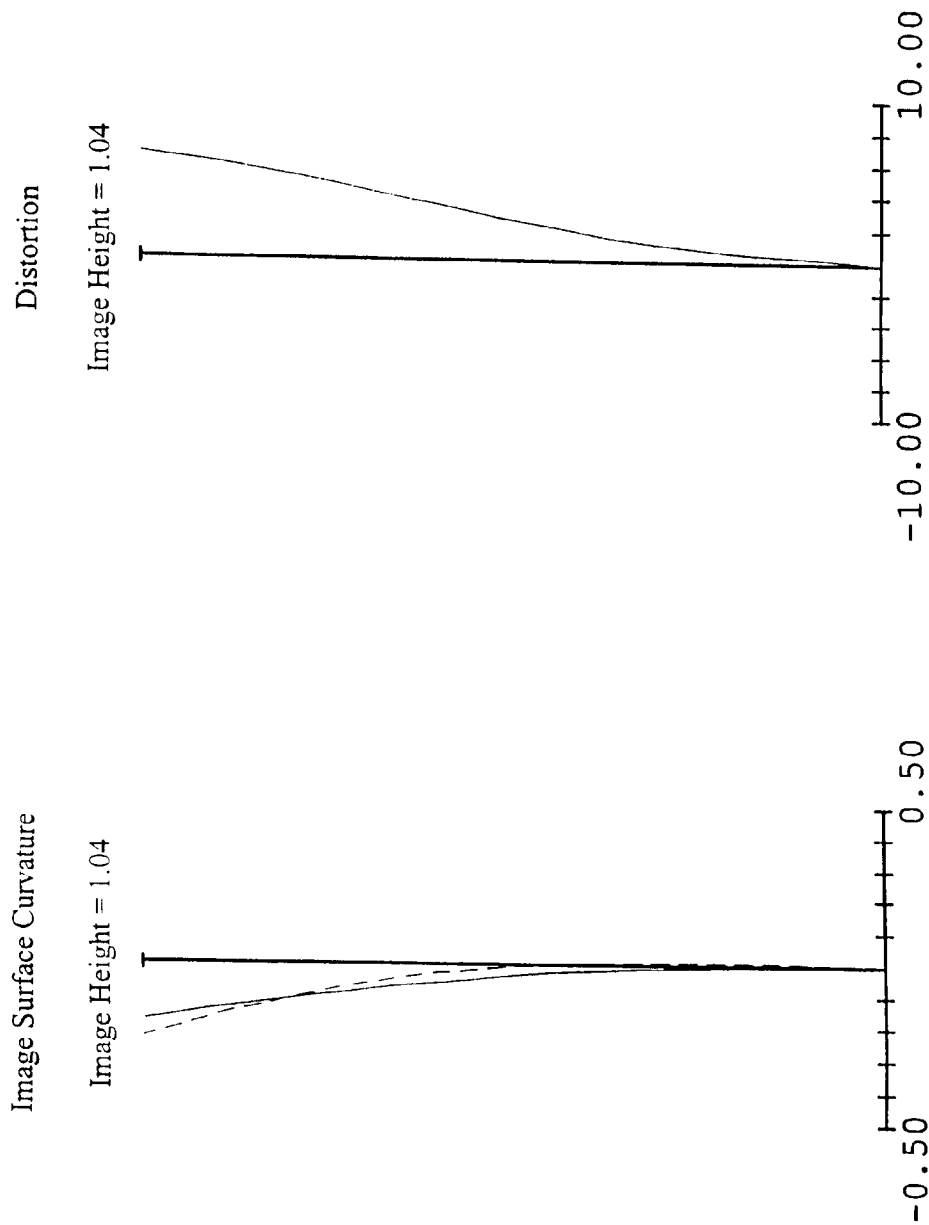

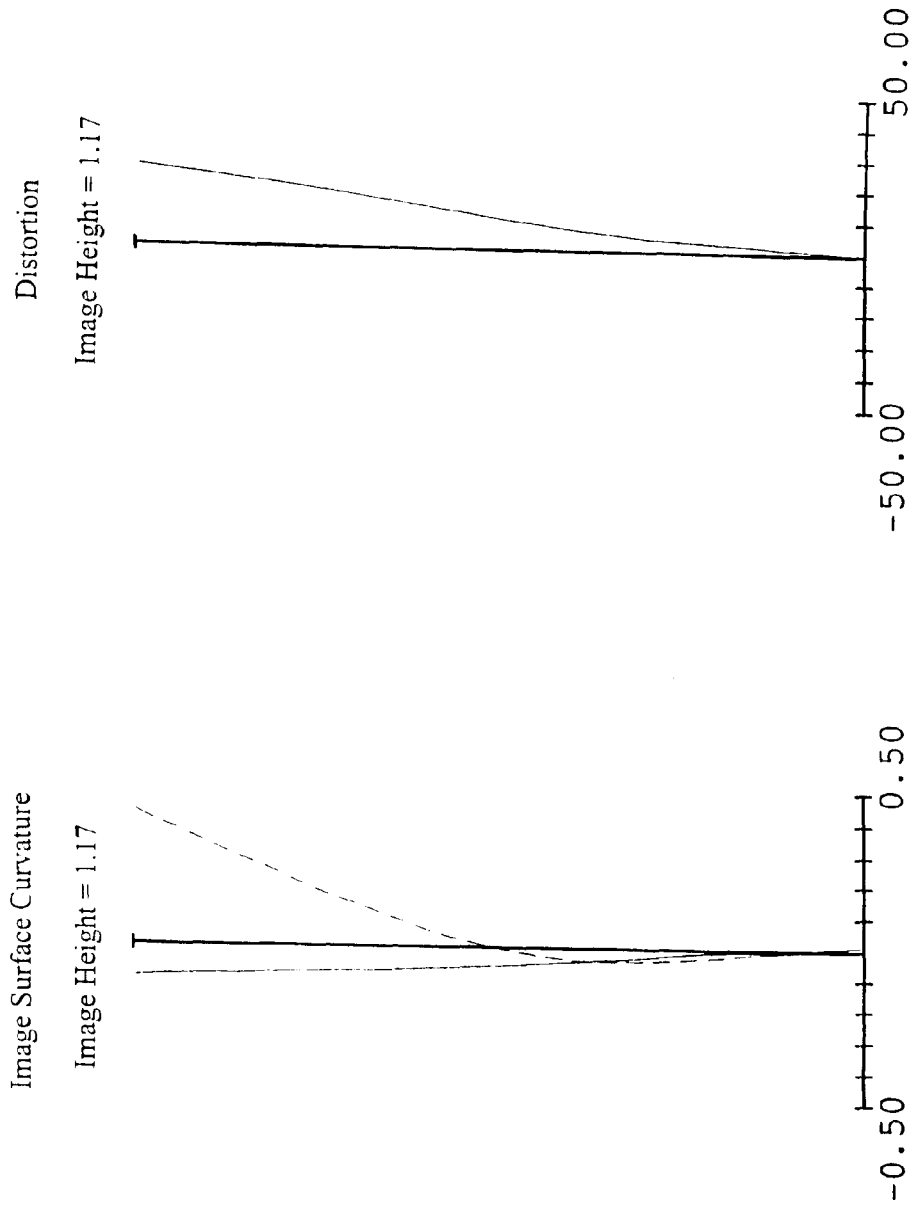

IMAGING OPTICAL SYSTEM AND ENDOSCOPE PROVIDED WITH IMAGING OPTICAL SYSTEM

CROSS REFERENCE TO RELATED APPLICATION

This is a divisional application of allowed U.S. application Ser. No. 11/941,502 filed Nov. 16, 2007, now U.S. Pat. No. 7,576,310 which application was a divisional application of U.S. application Ser. No. 11/401,358, filed Apr. 11, 2006, which issued as U.S. Pat. No. 7,317,180 on Jan. 8, 2008. The present application claims benefit of priority under 35 U.S.C. §119 of JP 2005-129,191, filed Apr. 27, 2005, the contents of which are hereby incorporated by reference.

BACKGROUND OF THE INVENTION

Endoscopes have become widely used in the medical and industrial fields. A capsule endoscope that integrates the imaging optical system into a capsule that can be swallowed has been used in the medical field. For instance, Japanese Laid-Open Patent Application 2003-260024 discloses one example of a capsule endoscope that includes an objective lens for forming an image of an object, a solid-state image sensor for converting the optical image into an electronic signal, and a light emitting diode for illuminating the object, all of which are integrated within a hemispherical or nearly hemispherical transparent cover.

Additionally, Japanese Laid-Open Patent Application 2003-5031 discloses an example in which a single aspheric lens element is used in the objective optical system so that production costs can be reduced and the imaging optical system can be miniaturized, which in turn generally enables producing a small electronic imaging device suitable for devices such as a cellular phone.

An imaging optical system that captures a good quality image that is small and suitable for viewing with an endoscope, and that also can be produced at a low cost, is demanded even in an endoscope wherein the imaging optical system is integrated into a hemispherical or nearly hemispherical transparent cover at the tip of, for example, a capsule endoscope. Unfortunately, however, if the imaging optical system described in Japanese Laid-Open Patent Application 2003-5031 were to be applied to this type of endoscope, a good quality image that is suitable for viewing with an endoscope would not be obtained although a reduction in cost could be achieved. The imaging optical system described in Japanese Laid-Open Patent Application 2003-5031 is designed as an optical system for capturing images of objects generally in an outdoor setting.

BRIEF SUMMARY OF THE INVENTION

The present invention relates to an imaging optical system having a spherical or nearly spherical viewing port and further relates to an endoscope using such an imaging optical system. Additionally, the present invention relates to an imaging optical system that can obtain a good quality image when viewing through an endoscope, as well as to an imaging optical system that can be made small and can be produced at low cost even when the imaging optical system is used in an endoscope having a spherical or nearly spherical viewing port.

BRIEF DESCRIPTION OF THE DRAWINGS

The present invention will become more fully understood from the detailed description given below and the accompanying drawings, which are given by way of illustration only and thus are not limitative of the present invention, wherein:

FIG. 5(a) shows astigmatism in terms of the curvatures of the sagittal and meridional image surfaces in relation to a Gaussian image surface according to Embodiment 1, and FIG. 5(b) shows distortion according to Embodiment 1;

FIG. 8(a) shows astigmatism in terms of the curvatures of the sagittal and meridional image surfaces in relation to a Gaussian image surface according to Embodiment 2, and FIG. 8(b) shows distortion according to Embodiment 2;

FIG. 10(a) shows astigmatism in terms of the curvatures of the sagittal and meridional image surfaces in relation to a Gaussian image surface according to Embodiment 3, and FIG. 10(b) shows distortion according to Embodiment 3;

FIG. 13(a) shows astigmatism in terms of the curvatures of the sagittal and meridional image surfaces in relation to a Gaussian image surface according to Embodiment 4, and FIG. 13(b) shows distortion according to Embodiment 4;

FIG. 20(a) shows astigmatism in terms of the curvatures of the sagittal and meridional image surfaces in relation to a Gaussian image surface according to Embodiment 7, and FIG. 20(b) shows distortion according to Embodiment 7;

FIG. 23(a) shows astigmatism in terms of the curvatures of the sagittal and meridional image surfaces in relation to a Gaussian image surface according to Embodiment 8, and FIG. 23(b) shows distortion according to Embodiment 8;

DETAILED DESCRIPTION

Figure 1:
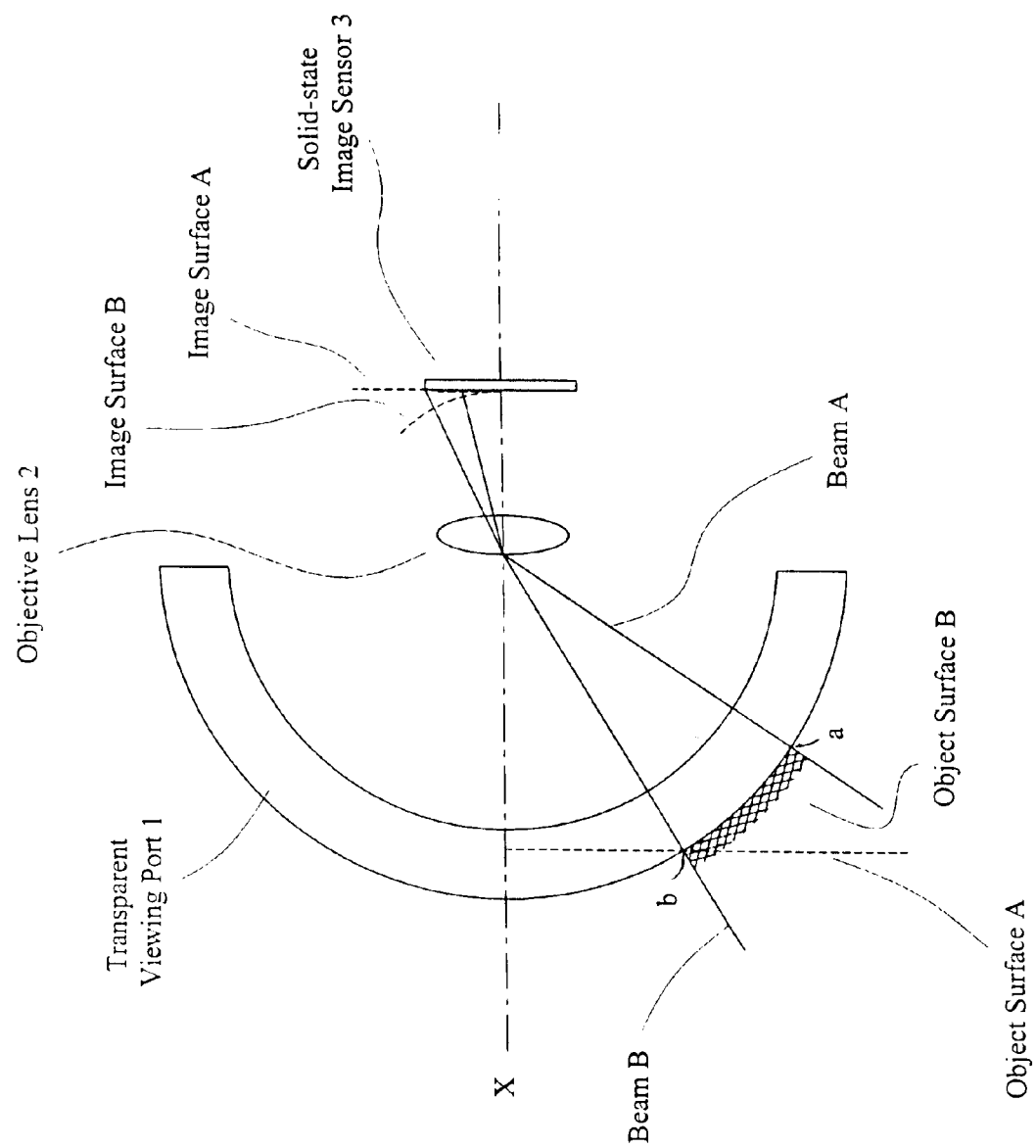
FIG. 1 is a cross-sectional view of an imaging optical system for explaining the nature of the present invention.

A viewing port having a spherical or nearly spherical shape is generally used in endoscopes for medical use, such as capsule endoscopes, that include a transparent viewing port in order to enable smooth insertion into a body cavity. The phrase "spherical or nearly spherical" is intended to include not only slight variations from a true spherical shape but also to include the viewing port being only part of a spherical shape generally, for example, forming a hemispherical or nearly hemispherical shape, which is descriptive of the invention as described more specifically below. When such an endoscope is inserted into a body cavity, the internal wall of the body cavity, which is the object for observation, is pressed against the viewing port. The peripheral part of the viewing port generally is in contact with the internal wall of the body cavity while the center part, or tip, of the viewing port generally is not in contact with the internal wall of the body cavity. In order to enable viewing of the internal wall of the body cavity accurately and safely in this state, the internal wall of the body cavity that is in contact with the peripheral part of the viewing port must be consistently brought into focus. An imaging optical system that includes an objective lens and a solid-state image sensor is arranged on the inside of the viewing port so that the central axis of the viewing port matches the optical axis of the imaging optical system. The objective lens optically forms an image of an object, which in this case is the internal wall of the body cavity. The solid-state image sensor converts this image into an electronic signal and includes an image-receiving surface that is perpendicular to the optical axis of the imaging optical system and that intersects the optical axis at the center of an effective imaging area of the image-receiving surface. When IH is the distance of the farthest point from the optical axis within the effective imaging area, the internal wall of the body cavity that is in contact with the peripheral part of the viewing port is placed within a viewing range defined by the distances from the optical axis between IH/2 and IH on the effective imaging area.

Generally, when an imaging optical system is applied, as described in Japanese Laid-Open Patent Application 2003-5031, the object surface defined by the internal wall portion in contact with the viewing port surface within the viewing range, as described above, is greatly curved. This is explained with reference to FIG. 1. The imaging optical system of FIG. 1 includes an objective lens 2 and a solid-state image sensor 3, and the image-receiving surface of the solid-state image sensor 3 is arranged on the Gaussian image surface of the objective lens 2. Additionally, the optical axis X of the imaging optical system is arranged to match the central axis of a spherical or nearly spherical viewing port 1. Beam A denotes a principal ray of the light beam that forms an image at the farthest point or position at the distance IH from the center of the effective imaging area within the effective imaging area of the image surface of the solid-state image sensor 3, and beam B denotes a principal ray of the light beam that forms an image at half of the distance IH of the farthest point or position from the center of the effective imaging area, in other words, at the point or position at the distance IH/2 from the center of the effective imaging area. Furthermore, an area where the point a at the intersection of beam A and the viewing port and the point b at the intersection of beam B and the viewing port are connected along the viewing port is defined as the object surface B within the viewing range determined by beam A and beam B. A plane that passes through the intersection point b and that is perpendicular to the optical axis X of the objective lens is defined as the object surface A.

Generally, an imaging optical system as disclosed in Japanese Laid-Open Patent Application 2003-5031 is constructed so that an object on an object plane at infinity can form an image on the image-receiving surface of the solid-state image sensor 3 that is arranged perpendicular to the optical axis of the objective lens 2. The image surface of a planar object that is arranged close to the objective lens 2, such as the object surface A, is also formed on a surface (image surface A, which is the image-receiving surface, in FIG. 1) that is perpendicular to the optical axis of the objective lens 2. Further, the image surface that corresponds to a curved object, such as the object surface B, which is arranged close to the objective lens 2 is formed on the highly curved surface (image surface B in FIG. 1) that extends toward the object side in relation to the image surface A that is perpendicular to the optical axis of the objective lens 2.

The position of the image-receiving surface of the solid-state image sensor along the optical axis can be varied about the exact focus position and still provide what is considered to be a focused image as long as the variation from the exact focus position along the optical axis is less than or equal to a value of $\Delta z$ that satisfies the following Condition:

$$|\Delta z|=n\cdot p/(\tan(\sin^{-1}(1/(2\cdot Fno)))) \quad \text{Condition (1)}$$

where the product $n\cdot p$ is the limit of resolution of the solid-state image sensor 3;

p is the pixel pitch of the solid-state image sensor 3;

n is a coefficient that is determined by the creation process of the luminance signal, with the value of this coefficient being determined by a circuit that processes the output of the solid state image sensor 3 and an electronic signal that is input to the solid-state image sensor 3; and Fno is the effective f-number of the entire imaging optical system.

The coefficient n has a value of about 4 for a single-panel type, solid-state image sensor. Additionally, the depth of focus of the imaging optical system is equal to $2\cdot|\Delta z|$.

As described above, there is a need to obtain an image that is in focus by using an imaging optical system so that at least one of a sagittal image surface and a meridional image surface that images the object surface B lies completely within a depth of focus in order for the imaging optical system to obtain the desired imaging of the object surface B for an endoscope having a spherical or nearly spherical viewing port. In particular, there is a need for the optical system formed of the transparent viewing port 1 and the objective lens 2 to use an objective lens 2 that results in at least one of the sagittal image surface and the meridional image surface related to an image of an object on the viewing port surface being formed so that one of the following Conditions related to $2\cdot|\Delta z|$ is satisfied:

$$\Delta S<2\cdot|\Delta z|=8\cdot p/\tan(\sin^{-1}(1/(2\cdot Fno)))) \quad \text{Condition (2)}$$

or $$\Delta M<2\cdot|\Delta z|=8\cdot p/(\tan(\sin^{-1}(1/(2\cdot Fno)))) \quad \text{Condition (2)'}$$

where $\Delta S$ is the distance in the direction of the optical axis between points of a sagittal image surface of the image at distances IH/2 and IH from the optical axis of the imaging optical system along straight lines perpendicular to the optical axis, and the point at the distance IH is the farthest point from the optical axis within an effective imaging area of the image-receiving surface centered on the optical axis of the imaging optical system;

$\Delta z$, p, and Fno are defined above; and $\Delta M$ is the distance in the direction of the optical axis between points of a meridional image surface of the image at distances IH/2 and IH from the optical axis of the imaging optical system along straight lines perpendicular to the optical axis, and the point at the distance IH is the farthest point from the optical axis within an effective imaging area of the image-receiving surface centered on the optical axis of the imaging optical system.

Figure 2:
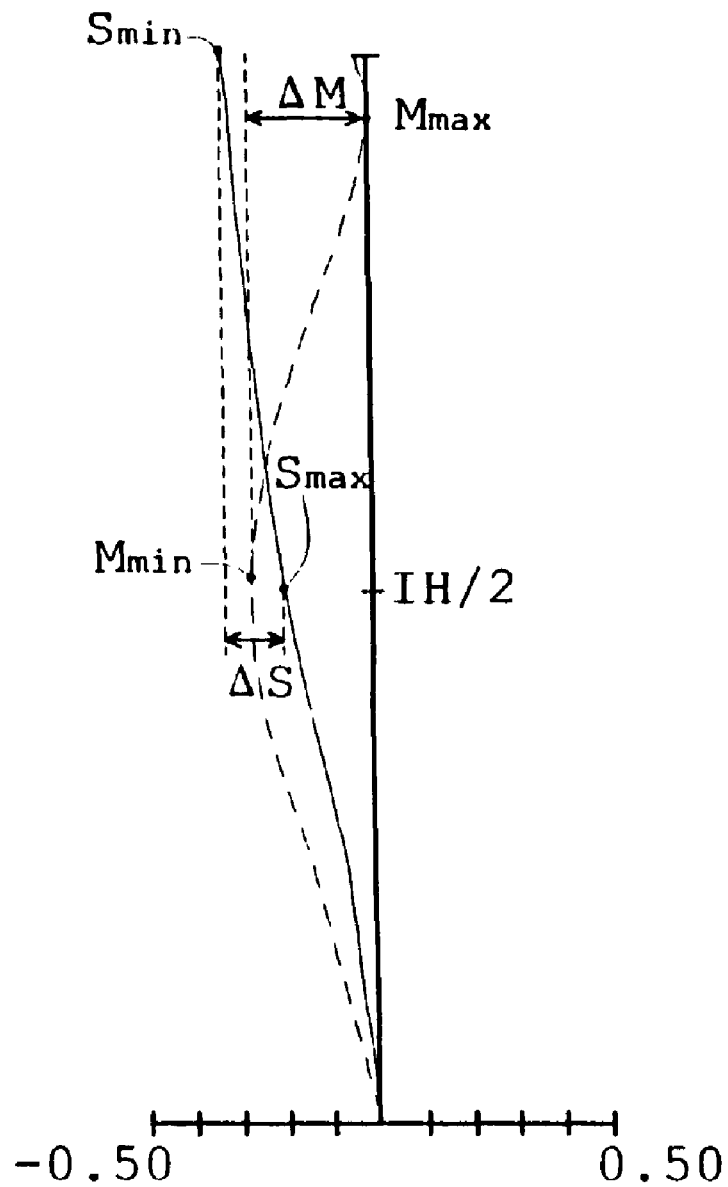
FIG. 2 shows aberrations related to explaining the present invention and particularly shows astigmatism in terms of the curvatures of the sagittal and meridional image surfaces in relation to a Gaussian image surface.

FIG. 2 shows the astigmatism of the imaging optical system in terms of the curvatures of the sagittal image surface (solid curved line) and the meridional image surface (dashed curved line) relative to a Gaussian image surface (solid straight line). In FIG. 2, the aberration curves extend to an image height of 1.07 mm, and the displacements (along the X-axis of the figure) are also expressed in millimeters. In FIG. 2, the points Smax, Smin, Mmax, and Mmin define image point locations of the sagittal and meridional image surfaces that are at different distances in the direction of the optical axis relative to the Gaussian image surface, and these points are used to define $\Delta S$ and $\Delta M$ as follows: $\Delta S$=Smax−Smin, $\Delta M$=Mmax−Mmin.

When considering details of the construction of an imaging optical system for an endoscope having a spherical or nearly spherical transparent viewing port, such as a capsule endoscope, the preferred construction is having the objective lens be a single lens element that includes an aspheric surface with a half-angle of view of fifty degrees or more and that is used with a solid-state image sensor having the common video signal format termed 'CIF format'. The term "lens element" is herein defined as a single transparent mass of refractive material having two opposed refracting surfaces, which surfaces are positioned at least generally transversely of the optical axis of the imaging optical system. Additionally, the pixel pitch of the solid-state image sensor should maintain about a seven micrometer standard when standardizing the focal length fL of an optical system that includes a transparent viewing port, and the effective aperture or f-number Fno of the imaging optical system must be 3.7 or less in order to ensure adequate brightness with the imaging optical system in combination with the use of a solid-state image sensor.

Accordingly, the focal depth (herein defined as $2\cdot|\Delta z|$, with $|\Delta z|$ as given in Condition (1) above) of the imaging optical system in units of millimeters is as set forth in the following Condition (3) when the features of the previous paragraph are applied:

$$2\cdot|\Delta z|=0.39 \text{ mm} \quad \text{Condition (3)}.$$

Furthermore, with the objective lens being a single lens element, in an imaging optical system as set forth above it is preferable that at least one of the sagittal image surface or meridional image surface satisfies a corresponding Condition (4) or (4)', respectively, within the range of the focal depth $2\cdot|\Delta z|$:

$$\Delta S/fL<0.4 \quad \text{Condition (4)}$$

or $$\Delta M/fL<0.4 \quad \text{Condition (4)'}$$

where fL is the focal length of the optical system that includes a transparent viewing port, and $\Delta S$ and $\Delta M$ are defined above.

Figure 3:
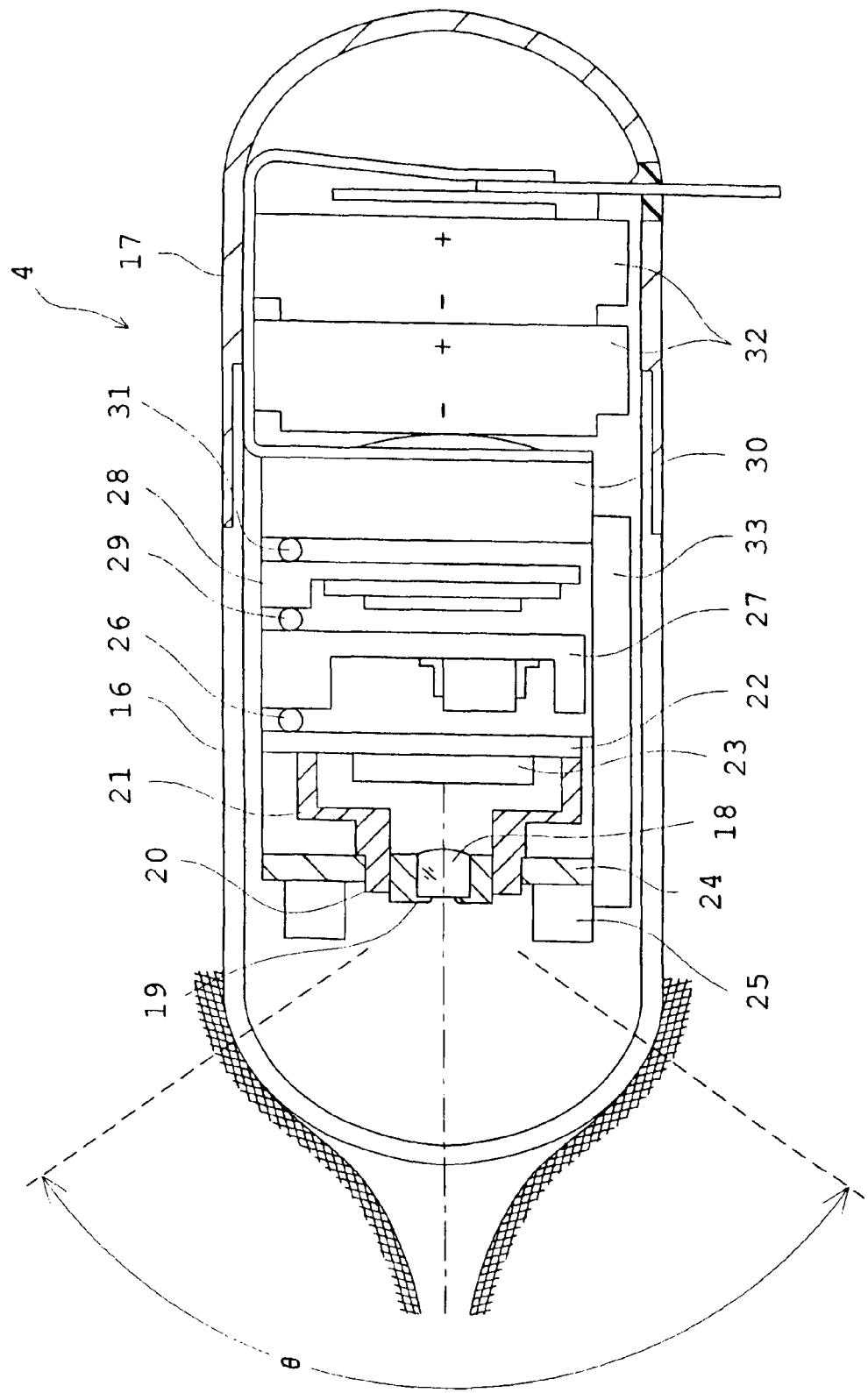
FIG. 3 is a cross-sectional view showing the internal construction of a capsule endoscope.

FIG. 3 is a cross-sectional view showing the internal construction of a capsule endoscope. As shown in FIG. 3, the capsule endoscope 4 includes an objective lens 18 and an LED 25 or similar device on the inner side of a transparent viewing port 16 that is sealed to a cover 17. The objective lens 18 is mounted on a lens frame 20 opposite the center part, or tip, of the viewing port 16, and an aperture stop diaphragm 19 (that is integrally formed with the lens frame 20) is arranged at the object-side surface of the objective lens 18. The lens frame 20 fits within a frame 21 mounted on a substrate 22 of the solid-state image sensor 23, and the assembly is cemented in place. Also, a plurality of LEDs 25 are mounted on a substrate 24, cemented in place, and fitted to the frame 21. An image sensor, such as a CCD, CMOS, or similar sensor, is used as the solid-state image sensor 23. Connection sections 26, 29, and 31 electrically connect the substrate 22 to a drive processing circuit 27, a memory circuit 28, and a wireless communication circuit 30, all of which are powered by button-type batteries 32. An antenna 33 is connected to the wireless communication circuit 30.

Ten embodiments of the present invention will now be discussed in detail with further reference to the drawings and with reference to various tables. In Tables 2-11 of Embodiments 1-10, respectively, the optical surfaces are labeled in numerical order under the heading "S" from the object-side surface of the viewing port. Thus, the object-side surface of the viewing port is surface "1", the image-side surface of the viewing port is surface "2", and so forth until the last optical surface, which is an image surface, is denoted as surface "7" in Tables 2-8 and as surface "8" in Tables 9-11. Various parameters of Embodiments 1-10 are also shown in Table 1 below, which has been divided into Part 1 for Embodiments 1-5 and Part 2 for Embodiments 6-10. In Table 1 below, each "x" in the bottom row indicates an embodiment where the meridional image surface has a large curvature such that ΔM exceeds 0.200 mm.

k is the eccentricity of the aspheric surface; and
A4, A6 ... $A_n$ are aspheric coefficients.

Embodiments 1-10 of the present invention will now be individually described with further reference to the drawings and to various tables.

EMBODIMENT 1

Figure 4:
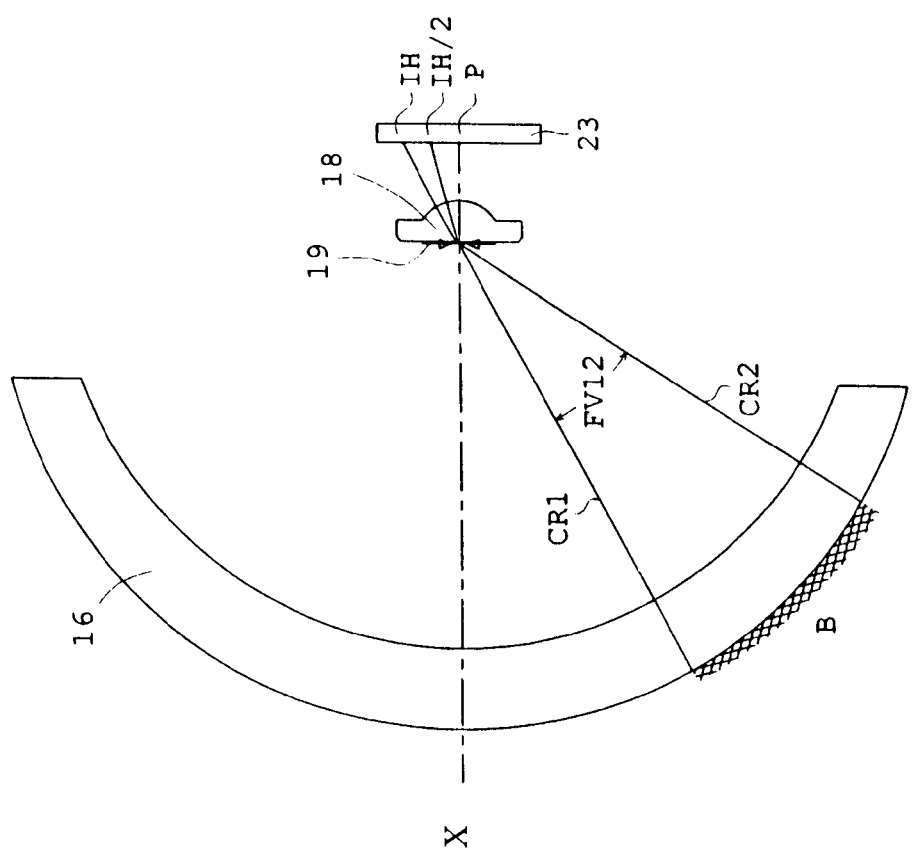
FIG. 4 is a cross-sectional view of an imaging optical system according to Embodiment 1.

Embodiment 1 is explained below with reference to FIGS. 4, 5(a), 5(b), and 6, as well as with reference to Table 2 below. FIG. 4 is a cross-sectional view of an imaging optical system according to Embodiment 1. FIG. 5(a) shows astigmatism in terms of the curvatures of the sagittal image surface (shown by a solid curved line) and the meridional image surface (shown by a dashed curved line) in relation to a Gaussian image surface (shown by a solid straight line) according to

TABLE 1

|  | Embodiment 1 | Embodiment 2 | Embodiment 3 | Embodiment 4 | Embodiment 5 |
|---|---|---|---|---|---|
| Radius of curvature of the flat surface side of the objective lens | INF | INF | INF | INF | INF |
| Radius of curvature of the convex surface side of the objective lens | −0.68117 | −0.68147 | −0.68115 | −0.69682 | −0.69418 |
| Thickness on the optical axis of the objective lens | 0.75829 | 0.88368 | 0.69033 | 0.56748 | 0.94003 |
| Eccentricity k of the aspheric surface | 0 | 0 | 0 | 0 | 0 |
| Aspheric coefficient A4 | 0.20276 | −0.6981 | 0.12136 | 0.38565 | −1.09502 |
| Aspheric coefficient A6 | 0.70237 | 2.31451 | 1.03779 | −0.39034 | 2.66146 |
| Aspheric coefficient A8 | 0 | −0.02542 | 0 | 0 | 0 |
| Focal length of the entire imaging system | 1.000 | 1.000 | 1.000 | 1.000 | 1.000 |
| Half-angle of view | −55.527 | −65.127 | −59.661 | −52.472 | −58.954 |
| Angle of incidence to the image surface | −26.702 | −23.223 | −29.562 | −32.178 | −16.398 |
| ΔS | 0.095 | 0.127 | 0.048 | 0.133 | 0.141 |
| ΔM | 0.059 | 0.258 | 0.191 | 0.196 | 0.308 |
|  |  | x |  |  | x |

|  | Embodiment 6 | Embodiment 7 | Embodiment 8 | Embodiment 9 | Embodiment 10 |
|---|---|---|---|---|---|
| Radius of curvature of the flat surface side of the objective lens | INF | 10.42047 | INF | INF | INF |
| Radius of curvature of the convex surface side of the objective lens | −0.68917 | −0.72818 | −0.58869 | −0.80769 | −0.80835 |
| Thickness on the optical axis of the objective lens | 0.63406 | 0.63567 | 1.50526 | 1.33135 | 1.32601 |
| Eccentricity k of the aspheric surface | 0 | 0 | −0.838 | −0.669 | −0.632 |
| Aspheric coefficient A4 | 0.10794 | 0.42107 | 0 | 0 | 0 |
| Aspheric coefficient A6 | 0.8249 | −0.4124 | 0 | 0 | 0 |
| Aspheric coefficient A8 | 0 | 0 | 0 | 0 | 0 |
| Focal length of the entire imaging system | 1.000 | 1.000 | 1.000 | 1.000 | 1.000 |
| Half-angle of view | −59.648 | −52.472 | −55.581 | −54.994 | −55.070 |
| Angle of incidence to the image surface | −29.935 | −31.447 | −16.280 | −14.375 | −15.723 |
| ΔS | 0.168 | 0.136 | 0.042 | 0.099 | 0.099 |
| ΔM | 0.081 | 0.220 | 0.430 | 0.058 | 0.058 |
|  |  | x | x |  |  |

In addition, the aspheric surface of the objective lens of each of Embodiments 1-10 is defined by the following Equation (A):

$$X = C \cdot S^2 / [1 + (1 - (k+1) \cdot C^2 \cdot S^2)^{1/2}] + A4 \cdot S^4 + A6 \cdot S^6 + \ldots + A_n \cdot S^n \quad \text{Equation (A)}$$

where

Figure 6:
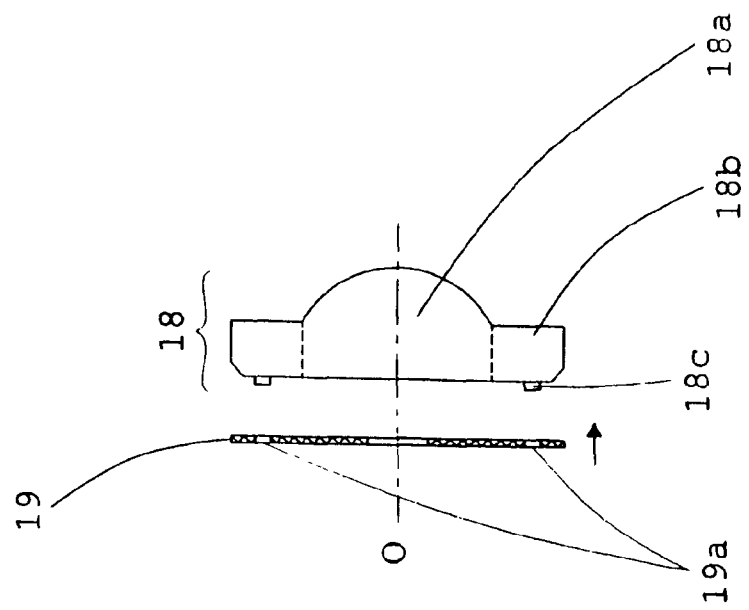
FIG. 6 shows a cross-sectional view of the diaphragm that serves as a stop and the objective lens of Embodiment 1 aligned for connecting together.

X is the length of a line segment from a point on the aspheric surface at a distance S from the optical axis measured perpendicular to the optical axis to the plane that is tangent to the vertex of the aspheric surface;

C=1/R where R is the radius of curvature of the aspheric surface on the optical axis;

Embodiment 1, and FIG. 5(b) shows distortion (in %) according to Embodiment 1. In FIGS. 5(a) and 5(b), the aberration curves extend to an image height of 1.03 mm, and in FIG. 5(a) the displacements (along the X-axis) are expressed in millimeters. Figures similar to FIGS. 5(a) and 5(b) will be used below to similarly describe Embodiments 2-10 of the present invention. FIG. 6 shows a cross-sectional view of the diaphragm that serves as an aperture stop and the objective lens of Embodiment 1 aligned for connecting them together. In addition, reference symbols common to FIGS. 3, 4, and 6 that are used to describe the construction of Embodiment 1 similarly describe the imaging optical systems of Embodiments 2-10 that will be described after Embodiment 1. Table 2 below shows optical design data of the imaging optical system of Embodiment 1. In Table 2, S is the surface number, RDY is the on-axis radius of curvature of this surface, THI is the on-axis surface separation between this surface and the next higher numbered surface, and Nd and Vd are the refractive index and Abbe number, respectively, (both measured at the d-line) of the material that follows this surface. INF indicates an infinite radius of curvature related to a planar surface. In this embodiment, the sixth surface (S6) is an aspheric surface with an eccentricity of zero, with only the aspheric coefficients A4 and A6 being non-zero, and with the values thereof being given in Table 1 above.

TABLE 2

| S | RDY | THI | Nd | Vd |
|---|---|---|---|---|
|  | 8.4974 (object surface) | 0.0000 |  |  |
| 1 | 8.4974 | 1.5450 | 1.51825 | 64.14 |
| 2 | 7.4159 | 7.4798 |  |  |
| 3 | INF (diaphragm) | 0.0000 |  |  |
| 4 | INF | 0.0400 |  |  |
| 5 | INF | 0.7583 | 1.70235 | 70.00 |
| 6 | −0.6812 (aspheric surface) | 1.0882 |  |  |
| 7 | INF (image surface) | 0.0000 |  |  |

As shown in FIG. 4, the imaging optical system of Embodiment 1 includes, arranged in order from the object side, a transparent viewing port 16 with a spherical surface, an objective lens 18 that is a single plano-convex lens element, and a solid-state image sensor 23. The angle of view (i.e., the field angle) is 110°. The convex surface side of the objective lens 18 is an aspheric surface, and a diaphragm 19 that serves as an aperture stop is arranged at the flat surface side. An image surface of an object surface B (hereinafter referred to simply as 'the object B' in the descriptions of all the embodiments) that is distributed along the surface of the viewing port 16 is formed in the vicinity of the image surface of the solid-state image sensor 23 within the effective imaging area of the image surface of the solid-state image sensor 23. The center of the effective imaging area is centered on the optical axis X of the imaging optical system. With the distance to the farthest point in the effective imaging area from the center P of the effective imaging area shown as IH in FIG. 4, the aspheric surface of the objective lens 18 has a curvature toward the periphery that is smaller than the on-axis curvature and has a form wherein the amount of deviation from the on-axis curvature increases between where a principal ray CR1 that defines one edge of the periphery of the viewing field of the field of view range FV12 traverses the aspheric surface for imaging at the distance IH/2 from the point P and where a principal ray CR2 that defines the other edge of the periphery of the viewing field in the field of view range FV12 traverses the aspheric surface for imaging at the distance IH from the point P. This increase in the amount of deviation also pertains to Embodiments 2-10 that follow and their descriptions include very similar drawing figures.

The image surface of the object B that is distributed along the surface of the viewing port 16 in the field of view range FV12 is formed as a nearly flat image surface with the sagittal image surface having a depth in the direction of the optical axis X of ΔS=0.095 mm and the meridional image surface having a depth in the optical axis direction of ΔM=0.059 mm. Thus, favorable viewing ability is achieved in the image, including in the periphery of the image.

In addition, the optically effective lens portion and the lens frame may be formed as an integral unit because the objective lens 18 of Embodiment 1 can be manufactured as molded glass, which enables the assembly time of the imaging unit to be reduced and the precision of assembly to be improved. For example, as shown in FIG. 6, a frame unit 18b may be formed with rotational symmetry about the optical axis O at the periphery of the effective lens portion 18a of the objective lens 18. Protrusions 18c are also formed in at least two places on the surface of the object side of the frame unit 18b. By so doing, the optical axis of the objective lens 18 and the central axis of the aperture stop diaphragm 19 can be easily aligned by fitting the protrusions 18c into alignment holes 19a arranged in the aperture stop diaphragm 19.

EMBODIMENT 2

Figure 7:
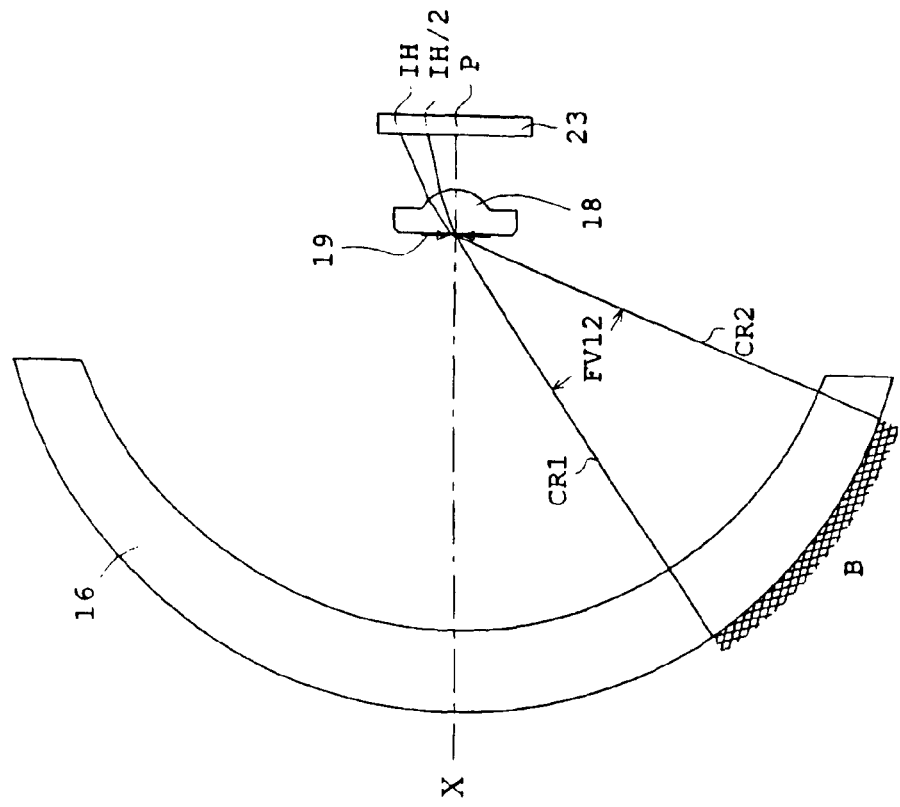
FIG. 7 is a cross-sectional view of an imaging optical system according to Embodiment 2.

Embodiment 2 is explained below with reference to FIGS. 7, 8(a), and 8(b), as well as with reference to Table 3 below. FIG. 7 is a cross-sectional view of an imaging optical system according to Embodiment 2. FIGS. 8(a) and 8 (b) show the astigmatism and distortion, respectively, for Embodiment 2 in the same manner that FIGS. 5(a) and 5(b) show the astigmatism and distortion, respectively, for Embodiment 1 as previously described. In Embodiment 2, the sixth surface (S6) is an aspheric surface with an eccentricity of zero, with only the aspheric coefficients A4, A6, and A8 being non-zero, and with the values thereof being given in Table 1 above.

TABLE 3

| S | RDY | THI | Nd | Vd |
|---|---|---|---|---|
|  | 8.8624 (object surface) | 0.0000 |  |  |
| 1 | 8.8624 | 1.6113 | 1.51825 | 64.14 |
| 2 | 7.7345 | 7.8011 |  |  |
| 3 | INF (diaphragm) | 0.0000 |  |  |
| 4 | INF | 0.0400 |  |  |
| 5 | INF | 0.8837 | 1.70235 | 70.00 |
| 6 | −0.6815 (aspheric surface) | 1.0826 |  |  |
| 7 | INF (image surface) | 0.0000 |  |  |

Although the basic construction of the imaging optical system of Embodiment 2 is the same as Embodiment 1, the angle of view is set to 130°. In the field of view range FV12 shown in FIG. 7, the aspheric surface of the objective lens 18 has a curvature toward the periphery that is larger than the on-axis curvature, and has a form having a point of inflection within the field of view range FV12. The image surface of the object B that is distributed along the surface of the transparent viewing port 16 in the field of view range FV12 is formed so that the sagittal image surface has a depth in the direction of the optical axis X of ΔS=0.127 mm and the meridional image surface has a depth in the direction of the optical axis X of ΔM=0.258 mm. Favorable viewing ability at the periphery of the image can be secured and focus adjustment also can be easily performed when the position of the image-receiving surface of the solid-state image sensor 23 is arranged with the ability to be adjusted in the optical axis direction with focusing being directed to focusing on the sagittal image surface that has less depth in the optical axis direction than the meridional image surface.

There is a need to construct the imaging optical systems of endoscopes for medical use with the ability to form images so that pathological changes that occur on a biological surface will not be overlooked. This is accomplished by providing a wide-angle field of view of 100° or more (preferably 130° or more). On the other hand, in order to enable viewing of an image of the object B that is distributed along the surface of the nearly spherical viewing port 16 by a single lens element as in the imaging optical system of the present invention, a form of aspheric surface that contributes to image formation is determined by concentrating on either one of the sagittal image surface or the meridional image surface, and the position of the image-receiving surface of the solid-state image sensor 23 in the direction of the optical axis X is preferably regulated in relation to the selected image surface. By so doing, a single lens element having an aspheric surface of a reasonable form that is easily produced can be achieved and focus adjustment is easily performed with a simple construction.

EMBODIMENT 3

Figure 9:
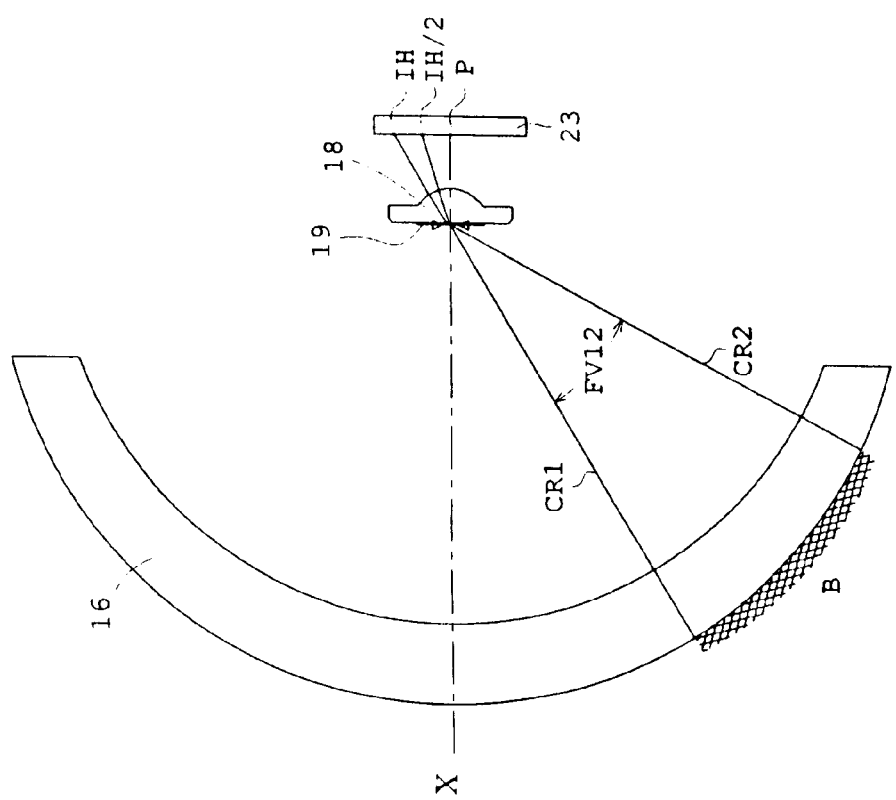
FIG. 9 is a cross-sectional view of an imaging optical system according to Embodiment 3.

Embodiment 3 is explained below with reference to FIGS. 9, 10(a), 10(b), 11(a) and 11(b), as well as with reference to Table 4 below. FIG. 9 is a cross-sectional view of an imaging optical system according to Embodiment 3. FIGS. 10(a) and 10(b) show the astigmatism and distortion, respectively, for Embodiment 3 in the same manner that FIGS. 5(a) and 5(b) show the astigmatism and distortion, respectively, for Embodiment 1 as previously described. In FIGS. 10(a) and 10(b), the aberration curves extend to an image height of 1.10 mm, and in FIG. 10(a) the displacements (along the X-axis) are expressed in millimeters. Table 4 below shows optical design data of the imaging optical system of Embodiment 3 in the same manner as Table 2 above shows optical design data of the imaging optical system of Embodiment 1. In Embodiment 3, the sixth surface (S6) is an aspheric surface with an eccentricity of zero, with only the aspheric coefficients A4 and A6 being non-zero, and with the values thereof being given in Table 1 above.

TABLE 4

| S | RDY | THI | Nd | Vd |
|---|---|---|---|---|
|  | 9.0446 (object surface) | 0.0000 |  |  |
| 1 | 9.0446 | 1.6445 | 1.51825 | 64.14 |
| 2 | 7.8934 | 7.9614 |  |  |
| 3 | INF (diaphragm) | 0.0000 |  |  |
| 4 | INF | 0.0400 |  |  |
| 5 | INF | 0.6903 | 1.70235 | 70.00 |
| 6 | −0.6812 (aspheric surface) | 1.0811 |  |  |
| 7 | INF (image surface) | 0.0000 |  |  |

Although the basic construction of the imaging optical system of Embodiment 3 is the same as Embodiment 1, the angle of view is set to 120°. Additionally, the objective lens 18 is the same as the objective lens of Embodiment 1 with regard to it being a single plano-convex lens element and having the same curvatures on the optical axis, that is, the same on-axis curvatures. In the field of view range FV12 shown in FIG. 9, the aspheric surface of the objective lens 18 has a curvature toward the periphery that is smaller than the on-axis curvature and has a form such that the amount of deviation from the on-axis curvature increases toward the periphery of the field of view. The image surface of the object B that is distributed along the surface of the transparent viewing port 16 in the field of view range FV12 is formed so that the sagittal image surface has a depth in the direction of the optical axis X of ΔS=0.048 mm and the meridional image surface has a depth in the direction of the optical axis X of ΔM=0.191 mm.

Figure 11B:
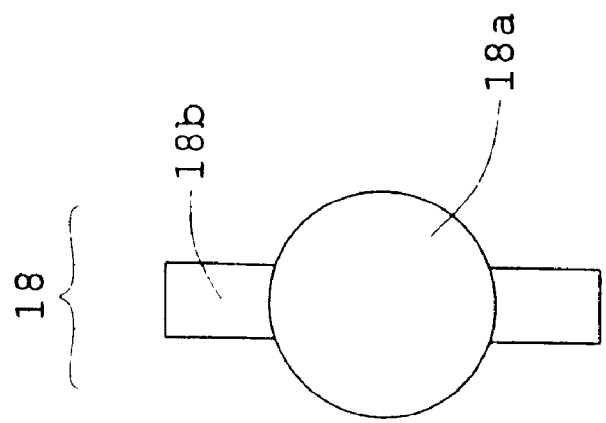
FIG. 11(b) shows a view from the image surface side of the objective lens of Embodiment 3.
Figure 11A:
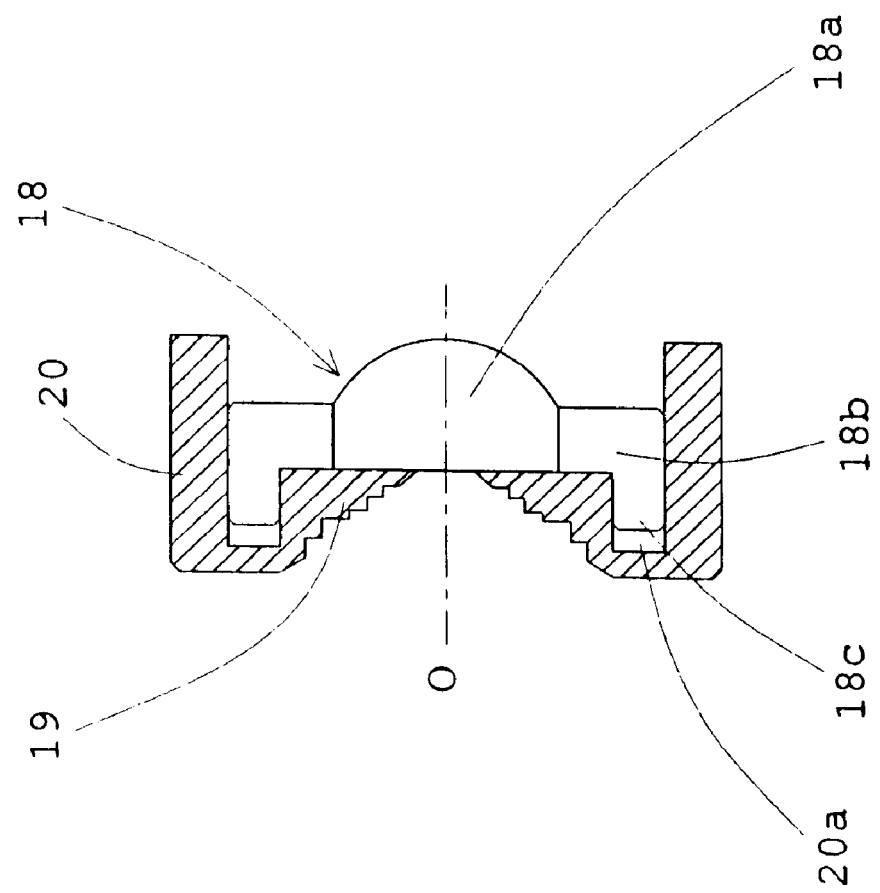
FIG. 11(a) shows a cross-sectional view of the objective lens and its lens frame of Embodiment 3 connected together.

FIG. 11(a) shows a cross-sectional view of the objective lens and the lens frame of Embodiment 3 connected together, and FIG. 11(b) shows a view from the image surface side of the objective lens of Embodiment 3. As shown in FIGS. 11(a) and 11(b), a pair of frame units 18b are formed symmetrically on opposite sides of the effective lens portion 18a of the objective lens 18 with a protrusion 18c on a surface of each of the pair of frame units 18b. Furthermore, an aperture stop diaphragm 19 and a lens frame 20 are integrally formed, the protrusions 18c are fitted into alignment holes 20a of the lens frame 20, and the diaphragm 19 is cemented in place inside the lens frame 20 so as to tightly connect the effective lens portion 18a and the diaphragm 19. An operation of assembling the objective lens 18 on the side of the lens frame 20 can be performed easily by using holding instruments such as forceps or a similar device. Furthermore, a central axis of the aperture stop diaphragm 19 can be easily aligned with the optical axis O of the objective lens 18 by fitting the protrusions 18c in the alignment holes 20a of the lens frame 20.

EMBODIMENT 4

Figure 12:
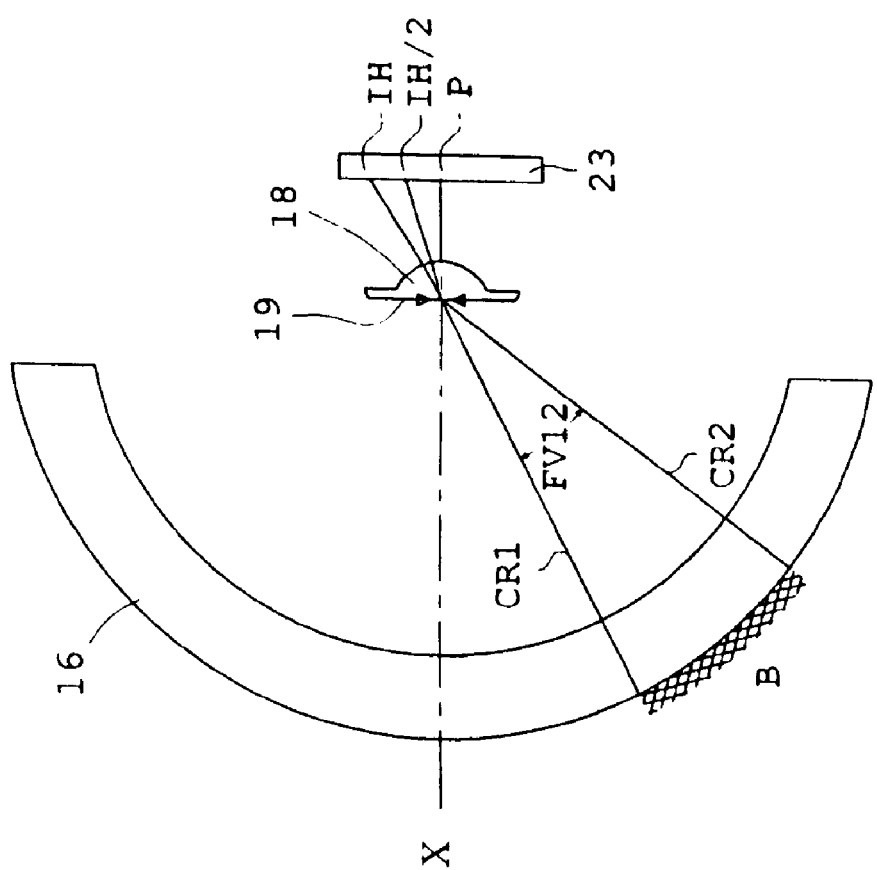
FIG. 12 is a cross-sectional view of an imaging optical system according to Embodiment 4.

Embodiment 4 is explained below with reference to FIGS. 12, 13(a), 13(b), 14(a), 14(b), and 14(c), as well as with reference to Table 5 below. FIG. 12 is a cross-sectional view of an imaging optical system according to Embodiment 4. FIGS. 13(a) and 13(b) show the astigmatism and distortion, respectively, for Embodiment 4 in the same manner that FIGS. 5(a) and 5(b) show the astigmatism and distortion, respectively, for Embodiment 1 as previously described. In FIGS. 13(a) and 13(b), the aberration curves extend to an image height of 1.04 mm, and in FIG. 13(a) the displacements (along the X-axis) are expressed in millimeters. Table 5 below shows optical design data of the imaging optical system of Embodiment 4 in the same manner as Table 2 above shows optical design data of the imaging optical system of Embodiment 1. In Embodiment 4, the sixth surface (S6) is an aspheric surface with an eccentricity of zero, with only the aspheric coefficients A4 and A6 being non-zero, and with the values thereof being given in Table 1 above.

TABLE 5

| S | RDY | THI | Nd | Vd |
|---|---|---|---|---|
|  | 6.5676 (object surface) | 0.0000 |  |  |
| 1 | 6.5676 | 1.2162 | 1.52765 | 56.25 |
| 2 | 5.3514 | 5.3514 |  |  |
| 3 | INF (diaphragm) | 0.0000 |  |  |
| 4 | INF | 0.0400 |  |  |
| 5 | INF | 0.5675 | 1.70235 | 70.00 |
| 6 | −0.6968 (aspheric surface) | 1.1734 |  |  |
| 7 | INF (image surface) | 0.0000 |  |  |

Embodiment 4 is an example of an imaging optical system suitable for being mounted in a small capsule endoscope. The imaging optical system of Embodiment 4 includes, arranged in order from the object side, a transparent viewing port 16 having spherical surfaces, an objective lens 18 that is a single plano-convex lens element, and a solid-state image sensor 23. The imaging optical system of Embodiment 4 has an angle of view of 104°. The convex surface side of the objective lens 18 is an aspheric surface, and an aperture stop diaphragm 19 is arranged at the planar surface side. In accordance with capsule miniaturization, the curvature of the viewing port 16 is larger relative to that of the imaging optical system of Embodiment 1, and for this reason, aberration correction by variations from a spherical surface in the objective lens 18 must be larger. In Embodiment 4, in the field of view range FV12 shown in FIG. 12, the aspheric surface of the objective lens 18 has a curvature toward the periphery that is smaller than the on-axis curvature and has a form such that the amount of deviation from the on-axis curvature increases toward the periphery of the field of view. The image surface of the object B that is distributed along the surface of the transparent viewing port 16 in the field of view range FV12 is formed so that the sagittal image surface has a depth in the direction of the optical axis X of ΔS=0.133 mm and the meridional image surface has a depth in the direction of the optical axis X of ΔM=0.196 mm. In this case, by the position of the image-receiving surface of the solid-state image sensor 23 being adjustable in the optical axis direction with focusing being directed to focusing on the sagittal image surface, favorable viewing ability at the periphery of the image can be achieved and focusing adjustment can be made easier.

Figure 14C:
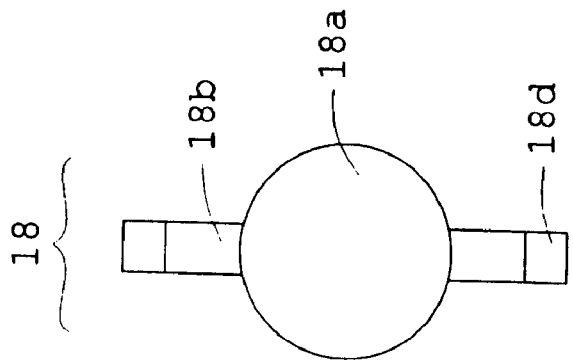
FIG. 14(c) shows an image side view of the objective lens of Embodiment 4.
Figure 14A:
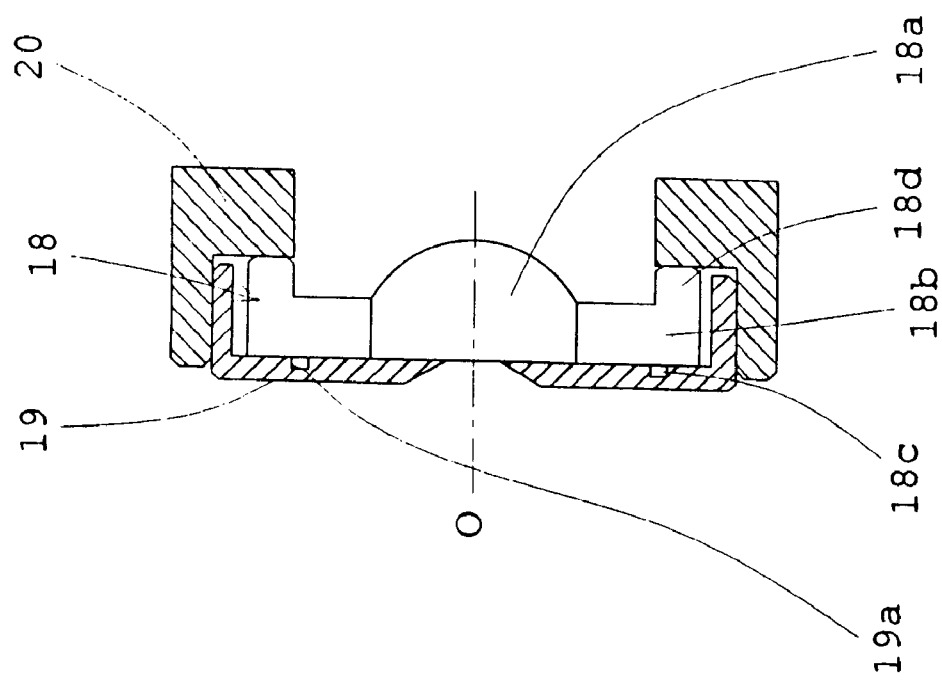
FIG. 14(a) shows a cross-sectional view of the objective lens and its lens frame of Embodiment 4 connected together.
Figure 14B:
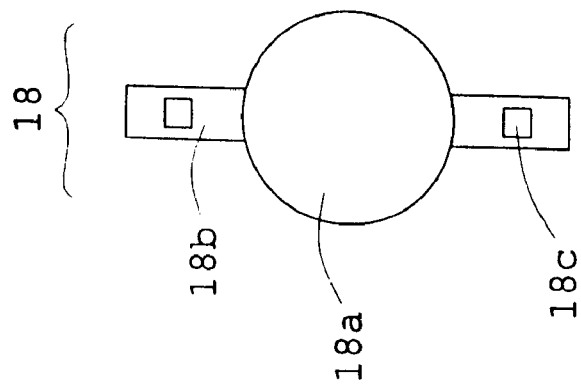
FIG. 14(b) shows an object side view of the objective lens of Embodiment 4.

FIG. 14(a) shows a cross-sectional view of the objective lens and its lens frame of Embodiment 4 connected together, FIG. 14(b) shows an object side view of the objective lens of Embodiment 4, and FIG. 14(c) shows an image side view of the objective lens of Embodiment 4. A pair of frame units 18b are formed symmetrically on opposite sides of the optical axis O of the objective lens 18 at the periphery of the effective lens unit 18a of the objective lens 18. Furthermore, protrusions 18c are formed on the object-side surfaces of these frame units 18b, and protrusions 18d are formed on the image-side surfaces of these frame units 18b. The protrusions 18c fit into alignment holes 19a in an aperture stop diaphragm 19 so that the effective lens unit 18a and the aperture stop diaphragm 19 are held tightly together. Additionally, the aperture stop diaphragm 19 fits in the lens frame 20 and is cemented in place to the inner side of the lens frame 20 with the protrusions 18d in contact with the lens frame 20.

EMBODIMENT 5

Figure 15:
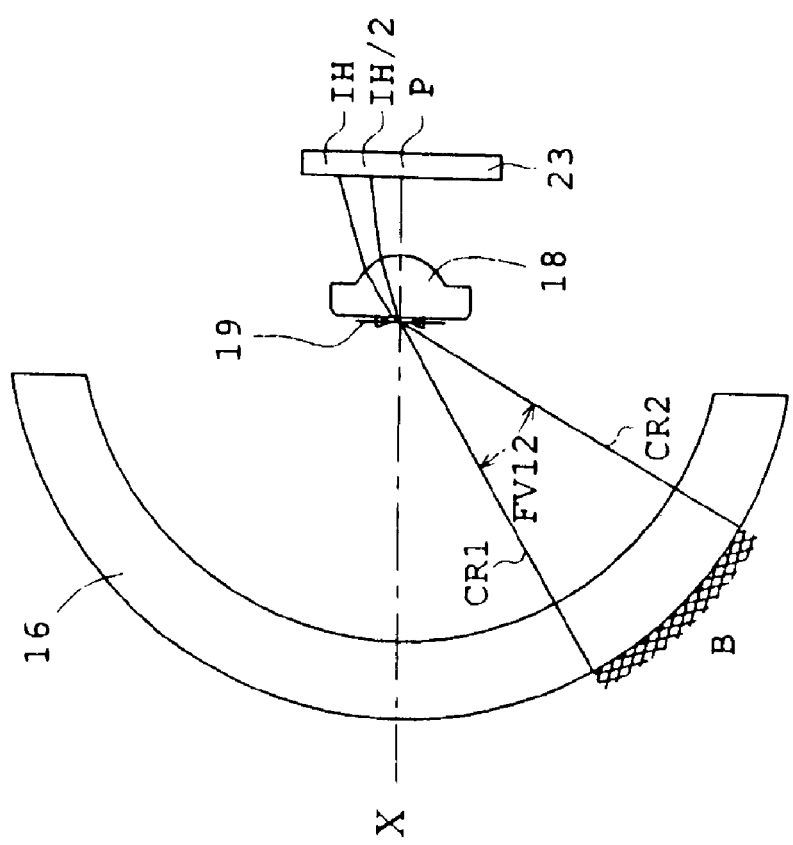
FIG. 15 is a cross-sectional view of an imaging optical system according to Embodiment 5.
Figure 16:
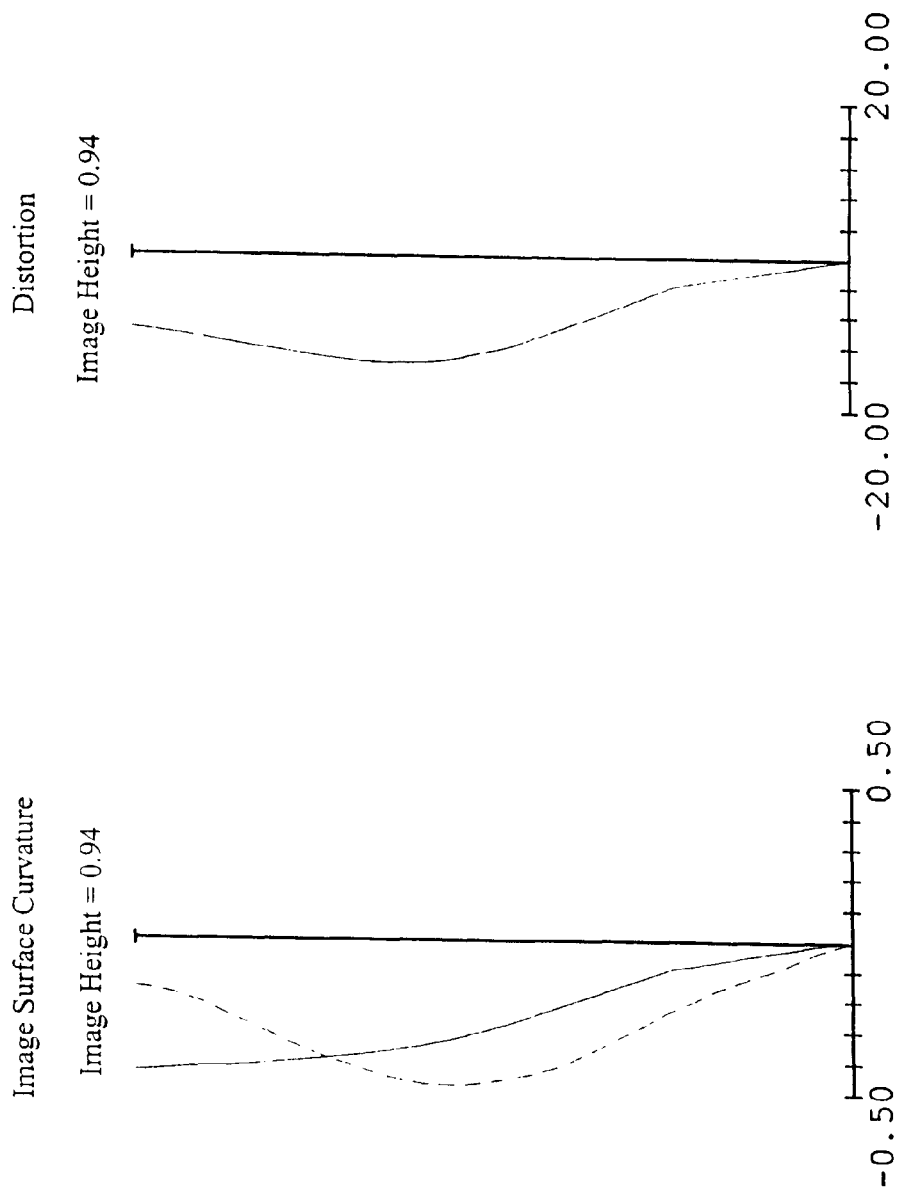
FIG. 16(a) shows astigmatism in terms of the curvatures of the sagittal and meridional image surfaces in relation to a Gaussian image surface according to Embodiment 5.
FIG. 16(b) shows distortion according to Embodiment 5.

Embodiment 5 is explained below with reference to FIGS. 15, 16(a), and 16(b), as well as with reference to Table 6 below. FIG. 15 is a cross-sectional view of an imaging optical system according to Embodiment 5. FIGS. 16(a) and 16(b) show the astigmatism and distortion, respectively, for Embodiment 5 in the same manner that FIGS. 5(a) and 5(b) show the astigmatism and distortion, respectively, for Embodiment 1 as previously described. Table 6 below shows optical design data of the imaging optical system of Embodiment 5 in the same manner as Table 2 above shows optical design data of the imaging optical system of Embodiment 1. In Embodiment 5, the sixth surface (S6) is an aspheric surface with an eccentricity of zero, with only the aspheric coefficients A4 and A6 being non-zero, and with the values thereof being given in Table 1 above.

TABLE 6

| S | RDY | THI | Nd | Vd |
|---|---|---|---|---|
|  | 5.9222 (object surface) | 0.0000 |  |  |
| 1 | 5.9222 | 1.1750 | 1.52765 | 56.25 |
| 2 | 4.8255 | 4.8255 |  |  |
| 3 | INF (diaphragm) | 0.0705 |  |  |
| 4 | INF | 0.0000 |  |  |
| 5 | INF | 0.9400 | 1.70235 | 70.00 |
| 6 | −0.6942 (aspheric surface) | 1.1773 |  |  |
| 7 | INF (image surface) | 0.0000 |  |  |

Although the basic construction of the imaging optical system of Embodiment 5 is the same as Embodiment 1, the angle of view is set to 118°. The objective lens 18 is a single piano-convex lens element with the convex surface being an aspheric surface. The image surface of the object B that is distributed along the surface of the transparent viewing port 16 in the field of view range FV12 is formed so that the sagittal image surface has a depth in the direction of the optical axis X of ΔS=0.141 mm and the meridional image surface has a depth in the direction of the optical axis X of ΔM=0.308 mm by having the aspheric surface of the objective lens 18 in the field of view range FV12 so as to have a larger curvature than the on-axis curvature and also by making the amount of deviation of curvature from the on-axis curvature so as to increase the curvature toward the periphery of the field of view. Favorable viewing ability at the periphery of the image can be secured and focus adjustment also can be easily performed when the position of the image-receiving surface of the solid-state image sensor 23 is arranged with the ability to be adjusted in the optical axis direction with focusing being directed to focusing on the sagittal image surface that has less depth in the optical axis direction than the meridional image surface.

EMBODIMENT 6

Figure 17:
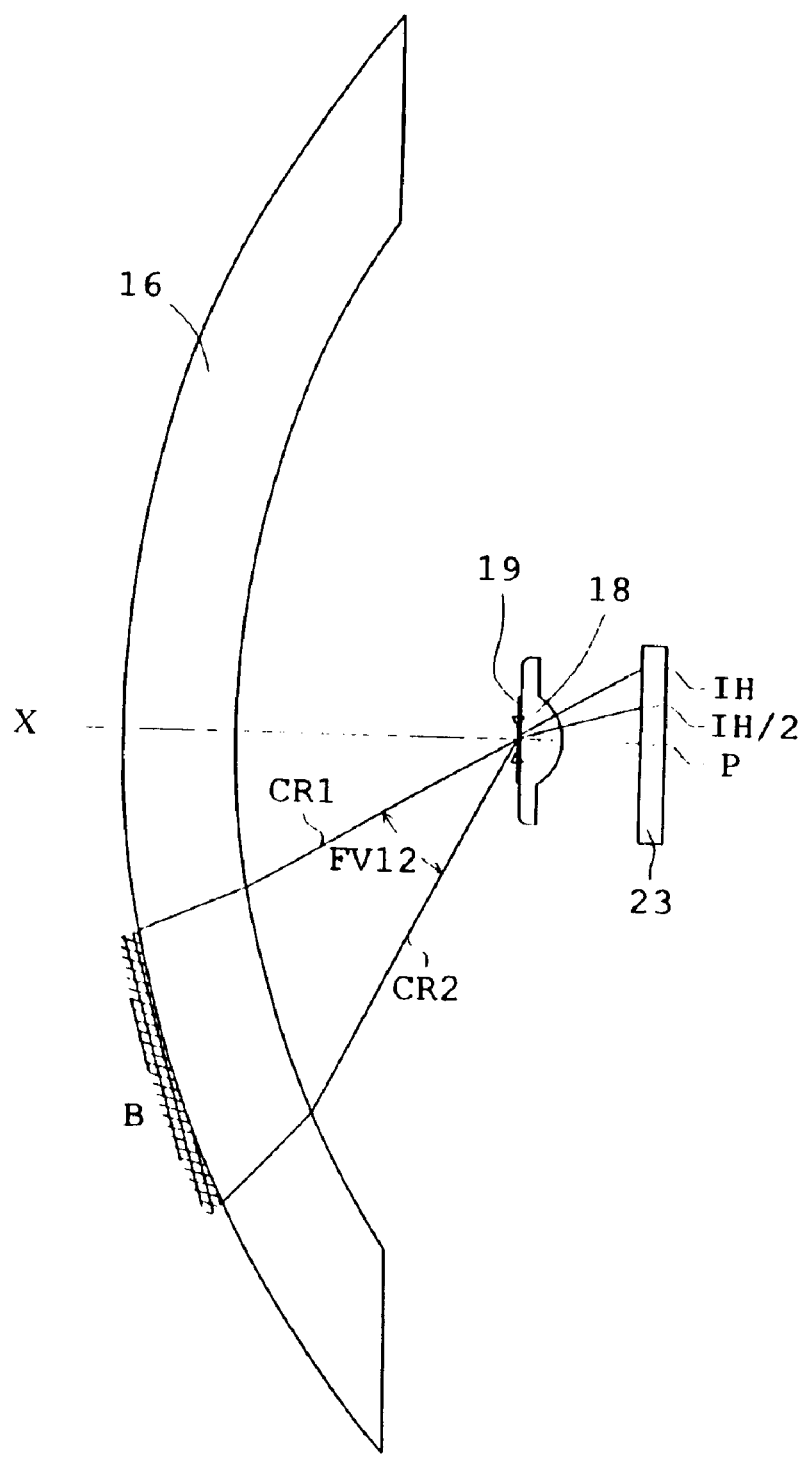
FIG. 17 is a cross-sectional view of an imaging optical system according to Embodiment 6.
Figure 18:
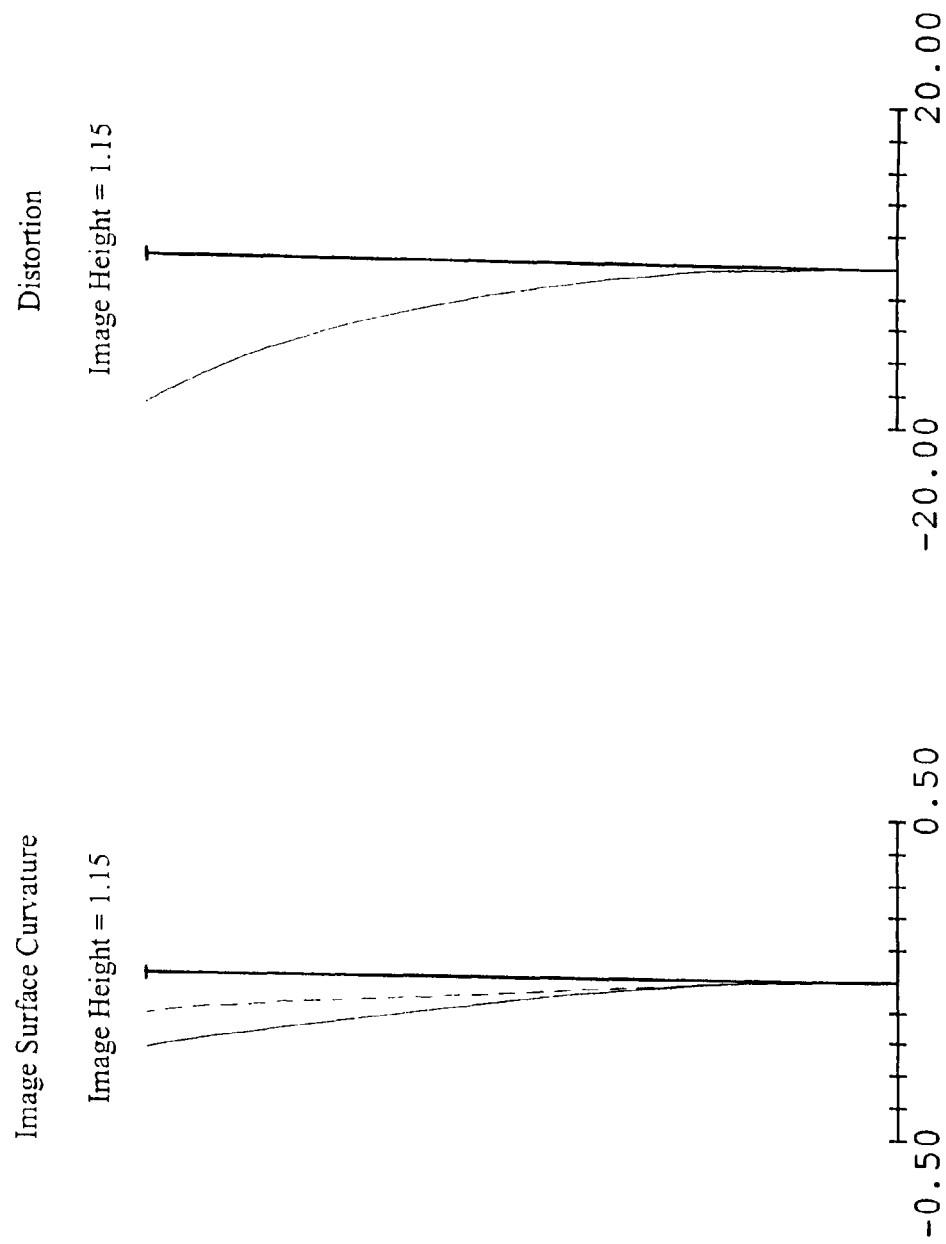
FIG. 18(a) shows astigmatism in terms of the curvatures of the sagittal and meridional image surfaces in relation to a Gaussian image surface according to Embodiment 6.
FIG. 18(b) shows distortion according to Embodiment 6.

Embodiment 6 is explained below with reference to FIGS. 17, 18(a), and 18(b), as well as with reference to Table 7 below. FIG. 17 is a cross-sectional view of an imaging optical system according to Embodiment 6. FIGS. 18(a) and 18(b) show the astigmatism and distortion, respectively, for Embodiment 6 in the same manner that FIGS. 5(a) and 5(b) show the astigmatism and distortion, respectively, for Embodiment 1 as previously described. Table 7 below shows optical design data of the imaging optical system of Embodiment 6 in the same manner as Table 2 above shows optical design data of the imaging optical system of Embodiment 1. In Embodiment 6, the sixth surface (S6) is an aspheric surface with an eccentricity of zero, with only the aspheric coefficients A4 and A6 being non-zero, and with the values thereof being given in Table 1 above.

TABLE 7

| S | RDY | THI | Nd | Vd |
|---|---|---|---|---|
|  | 17.1966 (object surface) | 0.0000 |  |  |
| 1 | 17.1966 | 1.7197 | 1.51825 | 64.14 |
| 2 | 14.6171 | 4.2992 |  |  |
| 3 | INF (diaphragm) | 0.0000 |  |  |
| 4 | INF | 0.0500 |  |  |
| 5 | INF | 0.6341 | 1.70235 | 70.00 |
| 6 | −0.6892 (aspheric surface) | 1.1806 |  |  |
| 7 | INF (image surface) | 0.0000 |  |  |

Embodiment 6 is an example of an imaging optical system that uses a spherical dome having a large radius of curvature as a transparent viewing port 16. The center of curvature of the dome is arranged on the optical axis of a plano-convex objective lens 18, and the angle of view is set to 120°. Furthermore, the convex surface of the objective lens 18 is an aspheric surface. In Embodiment 6, the image surface of the object B that is distributed along the surface of the viewing port 16 in the field of view range FV12 is formed so that the depth ΔS in the direction of the optical axis X of the sagittal image surface is 0.168 mm and the depth ΔM in the direction of the optical axis X of the meridional image surface is 0.081 mm by making the aspheric surface of the objective lens 18 in the field of view range FV12 so as to have a smaller curvature than the on-axis curvature and also by making the amount of deviation of curvature from the on-axis curvature larger toward the periphery of the viewing field. Favorable viewing ability at the periphery of the image can be obtained and focus adjustment can also be easily performed when the position of the image-receiving surface of the solid-state image sensor 23 is arranged with the ability to adjust the position in the optical axis direction while directing focusing to the meridional image surface that has a depth ΔM that is less than the depth ΔS of the sagittal image surface in the optical axis direction.

EMBODIMENT 7

Figure 19:
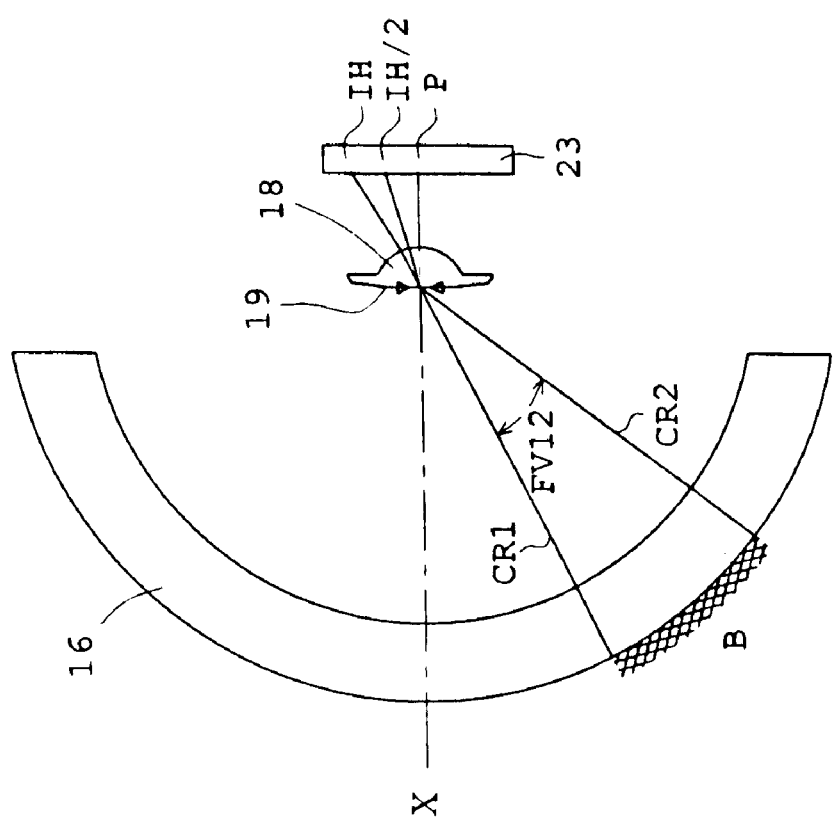
FIG. 19 is a cross-sectional view of an imaging optical system according to Embodiment 7.

Embodiment 7 is explained below with reference to FIGS. 19, 20 (a), 20(b), and 21, as well as with reference to Table 8 below. FIG. 19 is a cross-sectional view of an imaging optical system according to Embodiment 7. FIGS. 20(a) and 20(b) show the astigmatism and distortion, respectively, for Embodiment 7 in the same manner that FIGS. 5(a) and 5(b) show the astigmatism and distortion, respectively, for Embodiment 1 as previously described. Table 8 below shows optical design data of the imaging optical system of Embodiment 7 in the same manner as Table 2 above shows optical design data of the imaging optical system of Embodiment 1. In Embodiment 7, the sixth surface (S6) is an aspheric surface with an eccentricity of zero, with only the aspheric coefficients A4 and A6 being non-zero, and with the values thereof being given in Table 1 above.

TABLE 8

| S | RDY | THI | Nd | Vd |
|---|---|---|---|---|
|  | 5.5649 (object surface) | 0.0000 |  |  |
| 1 | 5.5649 | 1.2157 | 1.52765 | 56.25 |
| 2 | 5.3492 | 5.3492 |  |  |
| 3 | INF (diaphragm) | 0.0000 |  |  |
| 4 | INF | 0.0000 |  |  |
| 5 | 10.4205 | 0.6357 | 1.70235 | 70.00 |
| 6 | −0.7282 (aspheric surface) | 1.1481 |  |  |
| 7 | INF (image surface) | 0.0000 |  |  |

In Embodiment 7, an objective lens 18 is constructed as a single lens element having positive refractive power, a non-zero curvature on both surfaces, and with the image-side surface being an aspheric surface. The angle of view is set to 104°. Furthermore, the image surface of the object B that is distributed along the surface of the transparent viewing port 16 in the field of view range FV12 is formed so that the depth ΔS in the direction of the optical axis X of the sagittal image surface is 0.136 mm and the depth ΔM in the direction of the optical axis X of the meridional image surface is 0.22 mm by making the aspheric surface in the field of view range FV12 so as to have a smaller curvature than the on-axis curvature and also by making the amount of deviation of the curvature from the on-axis curvature become larger toward the periphery of the viewing field. Favorable viewing ability at the periphery of the image can be obtained and focus adjustment can also be easily performed when the position of the image-receiving surface of the solid-state image sensor 23 is arranged with the ability to adjust it in the optical axis direction and directing focusing to the sagittal image surface that has a depth ΔS that is less than the depth ΔM of the meridional image surface in the optical axis direction. Moreover, the object-side surface of the objective lens 18 is constructed so as to have positive refractive power, so that the effective diameter of the objective lens 18 can be smaller as a result of lowering the beam height in the field of view range FV12 on the aspheric surface. Consequently, technical properties of the objective lens can be improved by reducing the amount of deviation from the on-axis curvature in the periphery of the aspheric surface.

Figure 21:
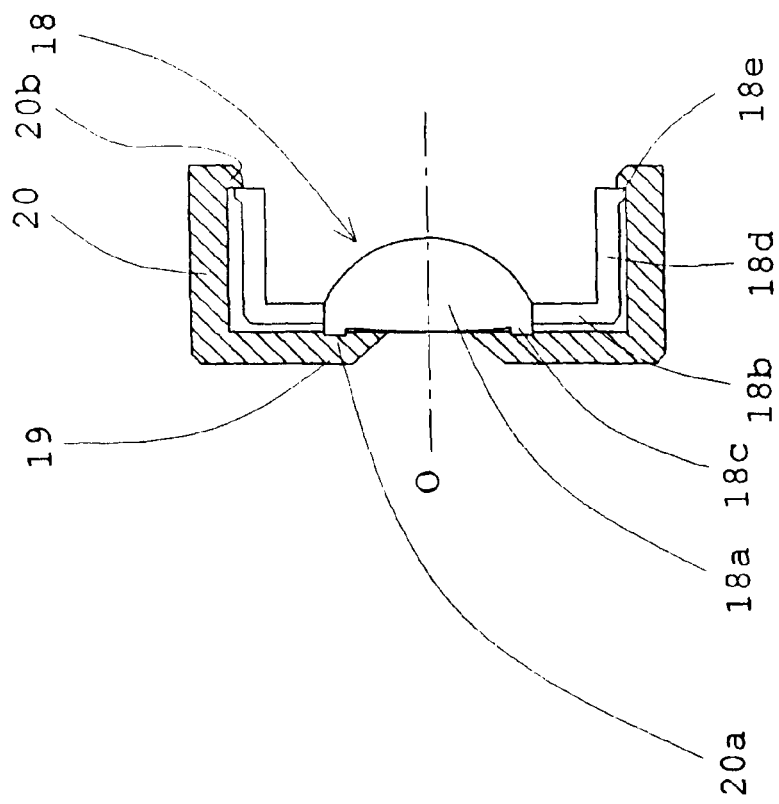
FIG. 21 is a cross-sectional view of the objective lens and the lens frame of Embodiment 7 connected together.

FIG. 21 is a cross-sectional view of the objective lens and the lens frame of Embodiment 7 connected together. In the objective lens 18, a pair of frame units 18b are formed symmetrically on opposite sides of the optical axis O of the objective lens 18 at the periphery of the effective lens unit 18a of the objective lens 18. Additionally, a protrusion 18c is formed rotationally symmetrically about the optical axis O on the object-side surface of the effective lens unit 18a. Furthermore, thin arm units 18d that can be bent inwardly and outwardly and that end in flanges 18e extend to the image side from the pair of frame units 18b. An aperture stop diaphragm 19 and a lens frame 20 are formed integrally as one unit, and the protrusion 18c fits into an alignment recess 20a. A flange 20b is arranged on the rim of the image side end of the lens frame 20, and the objective lens 18 is fixed on the inner side of the lens frame without adhesive by latching the flanges 18e and 20b in abutting contact. Assembling the objective lens 18 onto the inner side of the lens frame 20 is done by inserting the objective lens 18 into the inner side of the lens frame 20 until the protrusion 18c fits into the alignment recess 20a while the assembly is held by a tool such as a forceps, which avoids troublesome assembly procedures.

EMBODIMENT 8

Figure 22:
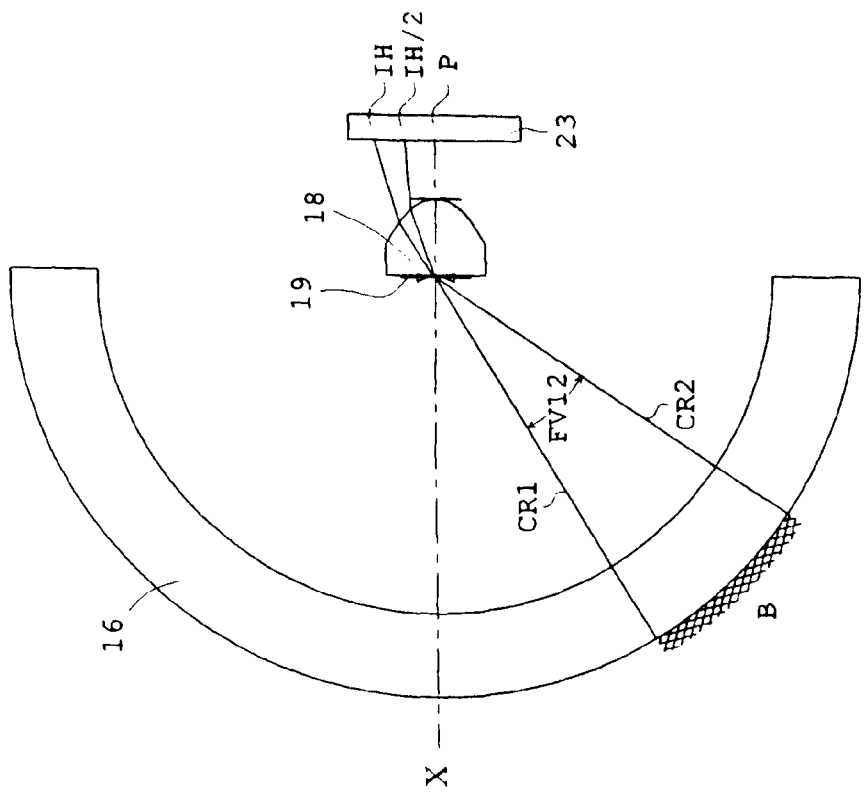
FIG. 22 is a cross-sectional view of an imaging optical system according to Embodiment 8.

Embodiment 8 is explained below with reference to FIGS. 22, 23(a), and 23(b), as well as with reference to Table 9 below. FIG. 22 is a cross-sectional view of an imaging optical system according to Embodiment 8. FIGS. 23(a) and 23(b) show the astigmatism and distortion, respectively, for Embodiment 8 in the same manner that FIGS. 5(a) and 5(b) show the astigmatism and distortion, respectively, for Embodiment 1 as previously described. Table 9 below shows optical design data of the imaging optical system of Embodiment 8 in the same manner as Table 2 above shows optical design data of the imaging optical system of Embodiment 1. In Embodiment 8, the sixth surface (S6) is an aspheric surface with a non-zero eccentricity, with all other aspheric coefficients (i.e., A2, A4, A6, etc.) being zero, and with the value of the eccentricity k being given in Table 1 above.

TABLE 9

| S | RDY | THI | Nd | Vd |
|---|---|---|---|---|
|  | 8.1970 (object surface) | 0.0000 |  |  |
| 1 | 8.1970 | 1.6394 | 1.58874 | 30.49 |
| 2 | 6.5576 | 6.5576 |  |  |
| 3 | INF (diaphragm) | 0.0447 |  |  |
| 4 | INF | 0.0000 |  |  |
| 5 | INF | 1.5053 | 1.58874 | 30.49 |
| 6 | −0.5887 (aspheric surface) | 0.0000 |  |  |
| 7 | INF | 1.1333 |  |  |
| 8 | INF (image surface) | 0.0000 |  |  |

The imaging optical system of Embodiment 8 includes, arranged in order from the object side, a transparent viewing port 16 with a spherical surface, an objective lens 18 that is a single plano-convex lens element, and a solid-state image sensor 23. The angle of view (i.e., the field angle) is 111°. The convex surface of the objective lens 18 is an ellipsoidal surface having rotational symmetry about the optical axis. An aperture stop diaphragm is arranged on the planar side of the objective lens 18.

The shape of the ellipsoidal surface of the objective lens 18 is determined by Equation (A) above using only the aspheric coefficient k, which is the eccentricity. That is, higher order aspheric coefficients, such as A4, A6, A8, etc., are zero in Equation (A) for this Embodiment 8. In this case, the eccentricity preferably satisfies the following Condition (5), and in Embodiment 8, the eccentricity k specifically equals −0.8380:

$$-0.6 < k < -0.85 \quad \text{Condition (5).}$$

The convex surface of the objective lens 18 of Embodiment 8 is an ellipsoid surface that is easy to trace, not an aspheric surface with a complicated form, so that technical properties of the objective lens can be improved. The ellipsoid surface has a curvature that decreases in the direction away from the optical axis, and the amount of deviation from the on-axis curvature in the periphery of the aspheric surface increases toward the periphery of the viewing field in the field of view range FV12.

It is necessary to consider the gate when designing a mold for casting plastic resin in order to properly form the objective lens of plastic material. In order to make the design related to the gate easier, the thickness D of the objective lens on the optical axis preferably satisfies the following Condition:

$$1.51 > D/fL > 0.94 \quad \text{Condition (6)}$$

where

D is the thickness of the objective lens at the center of the objective lens; and fL is the focal length of the entire imaging optical system.

In Embodiment 8, the thickness D of the objective lens at the center of the objective lens is 1.5 mm.

Along with the convex surface having an ellipsoidal shape, the thickness D of the objective lens 18 at its center, which is on the optical axis, is made relatively large, so that the angle of incidence Tw of a principal ray of the objective lens 18 can satisfy the following Condition (7) in relation to the image-receiving surface of the image sensor 23 for the light beam that forms an image on the image-receiving surface in the field of view range FV12:

$$|Tw| < 16.5° \quad \text{Condition (7).}$$

Having the angle of incidence Tw not satisfy Condition (7) is undesirable because in that case part of the incident light beam will be interrupted by the rim surrounding the image sensor, which decreases the amount of light passing to the image sensor. Also, too large an angle of incidence may result in light that should relate to a single pixel spanning two or more pixels on the image-receiving surface. Accordingly, the absolute value of the angle of incidence Tw of the principal ray related to the maximum image height position on the image-receiving surface of the image sensor 23 is 16.3° in Embodiment 8.

In addition, when the light beam is interrupted by a rim or similar structure, and the principal ray of an image at the maximum image height position on the image-receiving surface of the image sensor 23 cannot be defined, the angle of incidence may be defined by considering a light ray at a central position of the light beam to be a principal ray.

The image surface of the object B that is distributed along the surface of the transparent viewing port 16 in the field of view range FV12 is formed so that the depth ΔS in the direction of the optical axis X of the sagittal image surface is 0.042 mm and the depth ΔM in the direction of the optical axis X of the meridional image surface is 0.43 mm. The depth ΔM in the direction of the optical axis X of the meridional image surface does not satisfy Condition (1) above in this case; however, when the position of the image-receiving surface of the solid-state image sensor 23 is arranged so that focusing is directed to focusing of the sagittal image surface that has a depth ΔS equal to 0.042, favorable viewing ability at the periphery of an image can be ensured and the focus adjustment can also be performed easily.

EMBODIMENT 9

Figure 24:
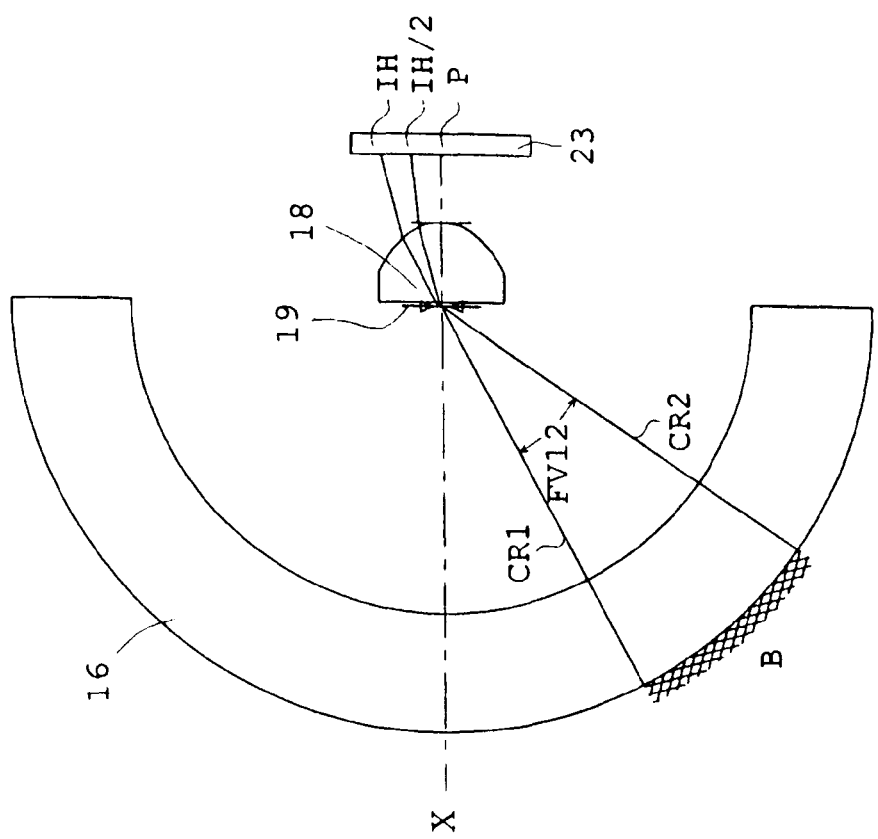
FIG. 24 is a cross-sectional view of an imaging optical system according to Embodiment 9.
Figures 25A, 25B:
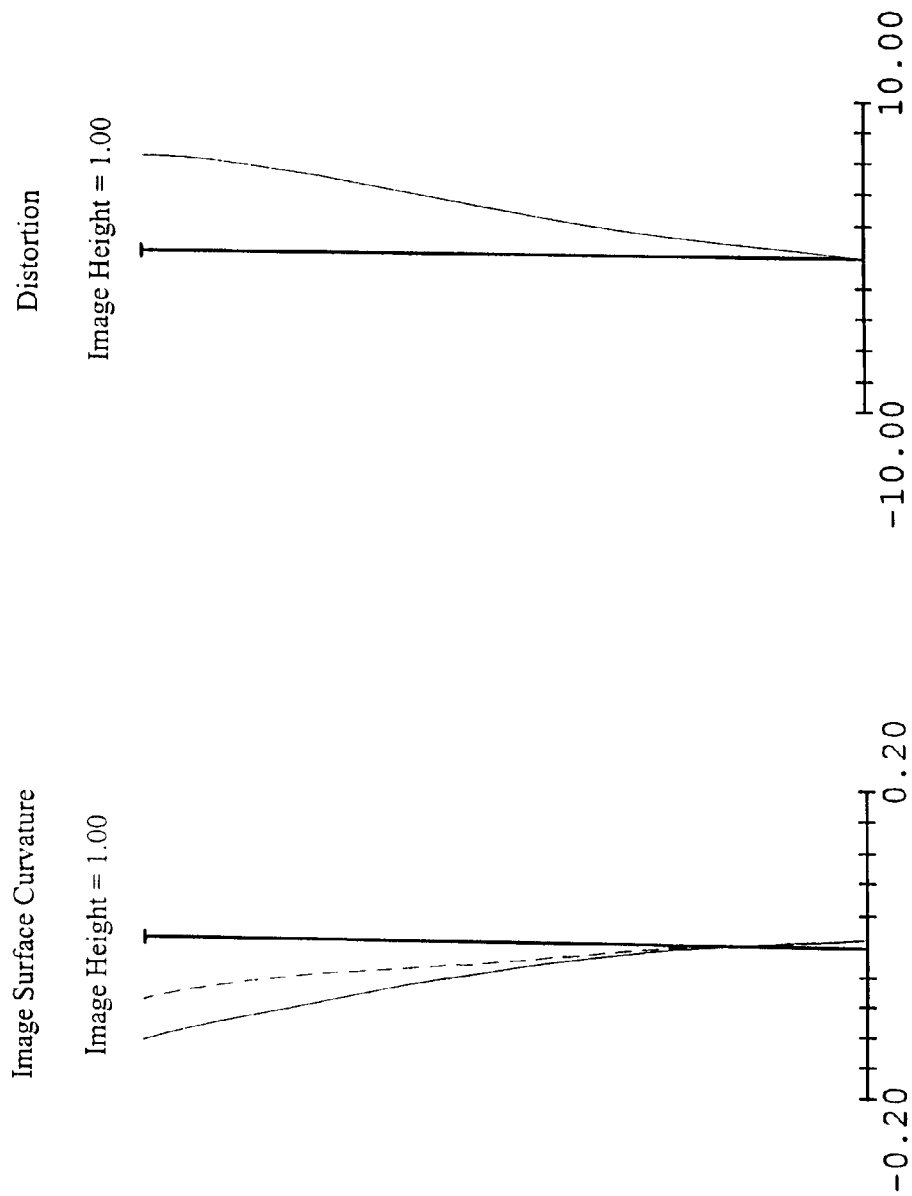
FIG. 25(a) shows astigmatism in terms of the curvatures of the sagittal and meridional image surfaces in relation to a Gaussian image surface according to Embodiment 9.
FIG. 25(b) shows distortion according to Embodiment 9.

Embodiment 9 is explained below with reference to FIGS. 24, 25(a), and 25(b), as well as with reference to Table 10 below. FIG. 24 is a cross-sectional view of an imaging optical system according to Embodiment 9. FIGS. 25(a) and 25(b) show the astigmatism and distortion, respectively, for Embodiment 9 in the same manner that FIGS. 5(a) and 5(b) show the astigmatism and distortion, respectively, for Embodiment 1 as previously described. Table 10 below shows optical design data of the imaging optical system of Embodiment 9 in the same manner as Table 2 above shows optical design data of the imaging optical system of Embodiment 1. In Embodiment 9, the sixth surface (S6) is an aspheric surface with a non-zero eccentricity, with all other aspheric coefficients (i.e., A2, A4, A6, etc.) being zero, and with the value of the eccentricity k being given in Table 1 above.

TABLE 10

| S | RDY | THI | Nd | Vd |
|---|---|---|---|---|
|   | 7.2115 (object surface) | 0.0000 |   |   |
| 1 | 7.2115 | 1.9970 | 1.58874 | 30.49 |
| 2 | 5.2145 | 5.2145 |   |   |
| 3 | INF (diaphragm) | 0.0666 |   |   |
| 4 | INF | 0.0000 |   |   |
| 5 | INF | 1.3314 | 1.81078 | 40.88 |
| 6 | −0.8077 (aspheric surface) | 0.0000 |   |   |
| 7 | INF | 1.1583 |   |   |
| 8 | INF (image surface) | 0.0000 |   |   |

Although the basic construction of the imaging optical system of Embodiment 9 is the same as Embodiment 8, the angle of view is set to 110°. In Embodiment 9, the convex surface of the plano-convex objective lens 18 is an ellipsoidal surface having rotational symmetry about the optical axis, and the eccentricity of the convex surface is −0.6690. The ellipsoidal surface of the objective lens 18 in the field of view range FV12 has a larger curvature than the on-axis curvature, and the ellipsoidal surface has a curvature with the amount of deviation from the on-axis curvature becoming larger toward the periphery of the periphery of the viewing field. The image surface of the object B that is distributed along the surface of the transparent viewing port 16 in the field of view range FV12 is formed so that the depth ΔS in the direction of the optical axis X of the sagittal image surface is 0.099 mm and the depth ΔM in the direction of the optical axis X of the meridional image surface is 0.058 mm by making the aspheric surface in the field of view range FV12. Favorable viewing ability at the periphery of the image can be obtained and focus adjustment can also be easily performed when the position of the image-receiving surface of the solid-state image sensor 23 is arranged with the ability to adjust it in the optical axis direction and directing focusing to the meridional image surface in this case. In addition, the thickness of the objective lens at its center on the optical axis is 1.33 mm and the absolute value of the angle of incidence Tw related to the maximum image height position on the image-receiving surface of the image sensor 23 is 14.4°.

EMBODIMENT 10

Figure 26:
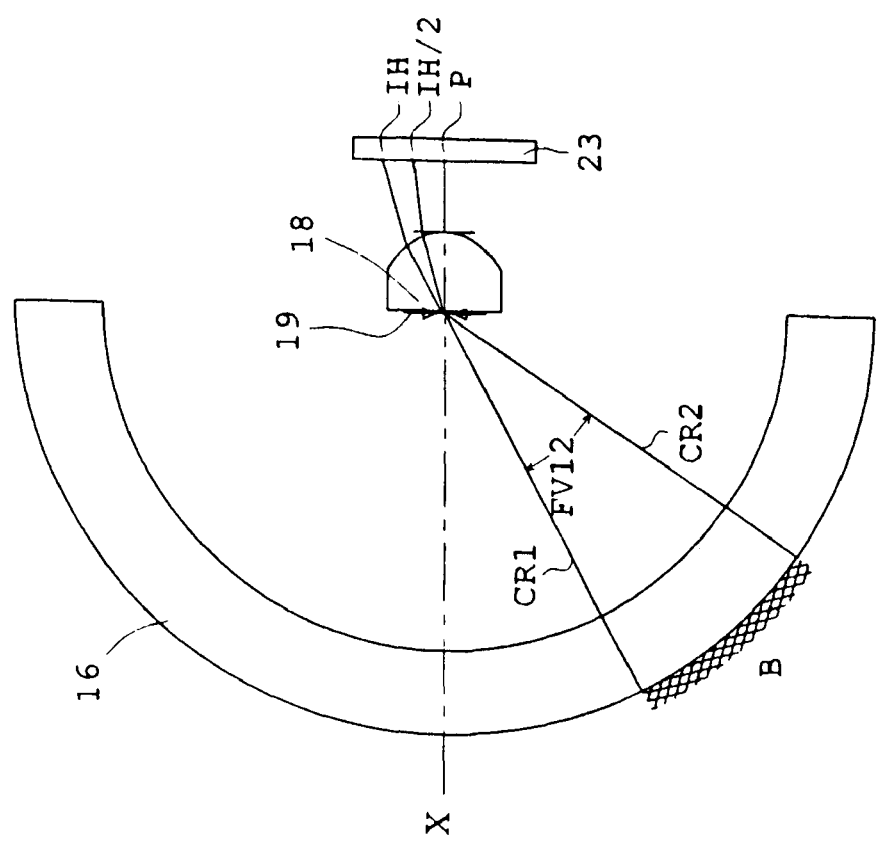
FIG. 26 is a cross-sectional view of an imaging optical system according to Embodiment 10.
Figure 27:
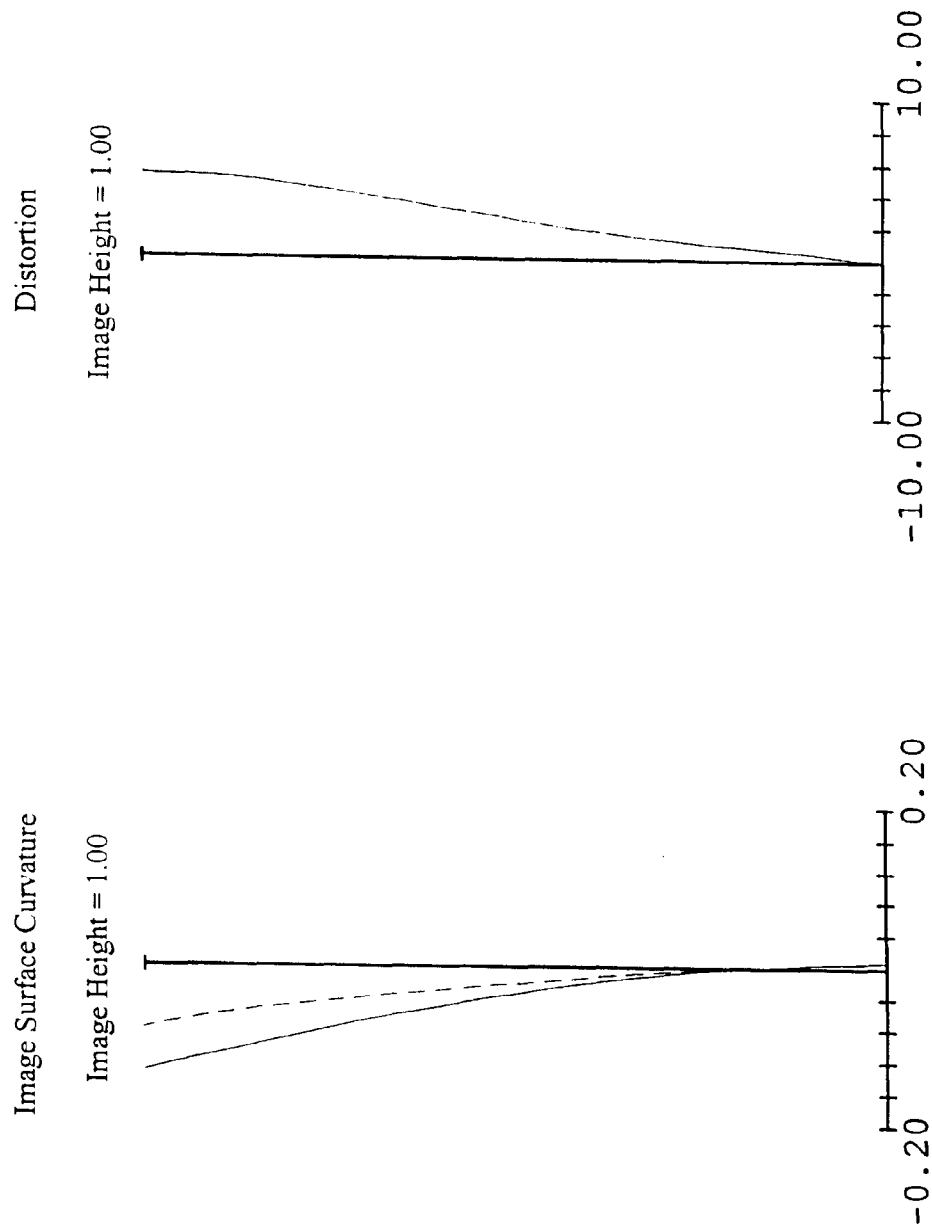
FIG. 27(a) shows astigmatism in terms of the curvature of the sagittal and meridional image surfaces in relation to a Gaussian image surface according to Embodiment 10.
FIG. 27(b) shows distortion according to Embodiment 10.
Figure 28:
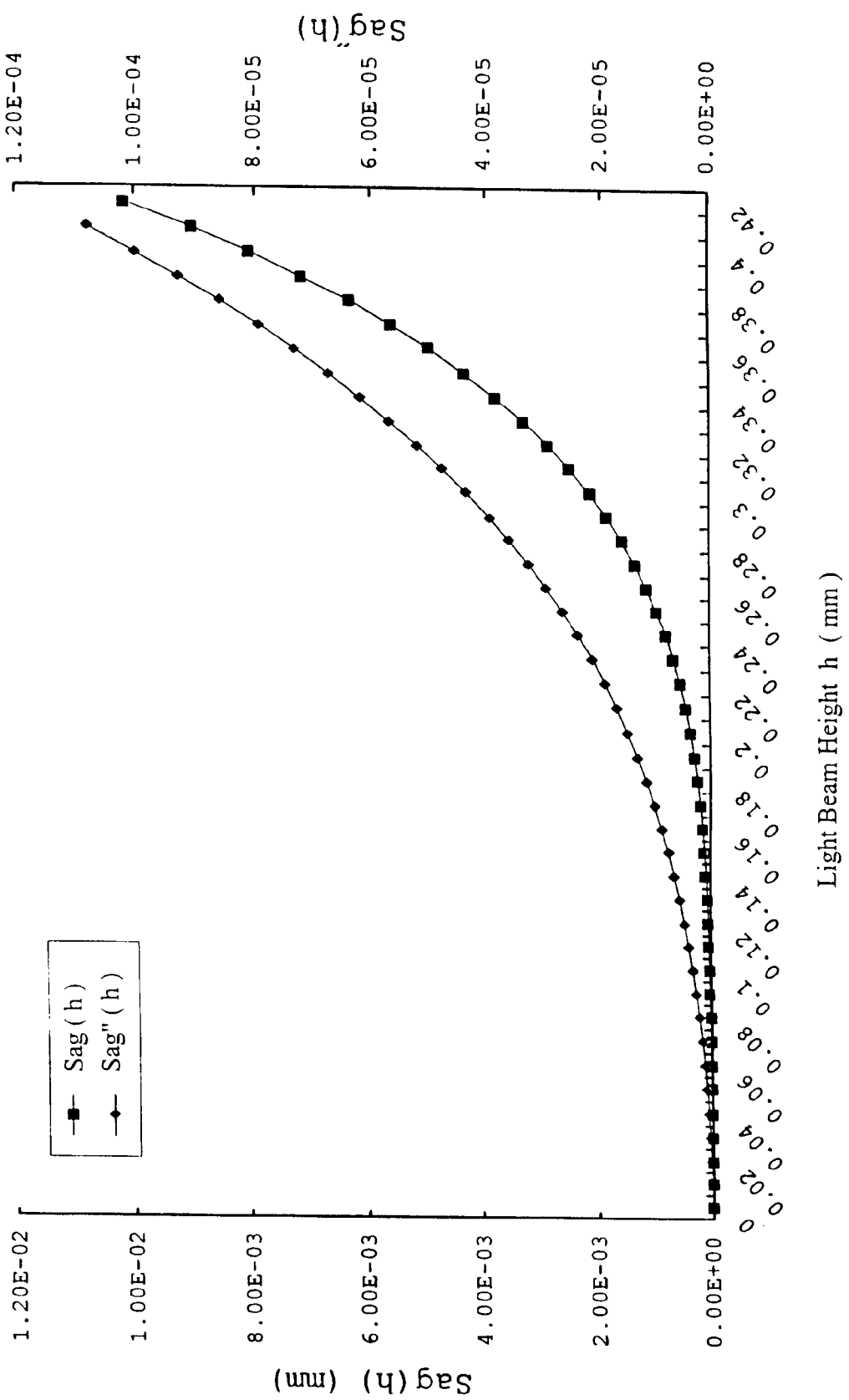
FIG. 28 is a graph showing the aspheric displacement and the second derivative of the aspheric displacement of the aspheric surface of the objective lens of Embodiment 1.

Embodiment 10 is explained below with reference to FIGS. 26, 27(a), and 27(b), as well as with reference to Table 11 below. FIG. 26 is a cross-sectional view of an imaging optical system according to Embodiment 10. FIGS. 27(a) and 27(b) show the astigmatism and distortion, respectively, for Embodiment 10 in the same manner that FIGS. 5(a) and 5(b)

show the astigmatism and distortion, respectively, for Embodiment 1 as previously described. Table 11 below shows optical design data of the imaging optical system of Embodiment 10 in the same manner as Table 2 above shows optical design data of the imaging optical system of Embodiment 1. In Embodiment 10, the sixth surface (S6) is an aspheric surface with a non-zero eccentricity, with all other aspheric coefficients (i.e., A2, A4, A6, etc.) being zero, and with the value of the eccentricity k being given in Table 1 above.

TABLE 11

| S | RDY | THI | Nd | Vd |
|---|---|---|---|---|
|  | 7.0125 (object surface) | 0.0000 |  |  |
| 1 | 7.0125 | 1.4025 | 1.58874 | 30.49 |
| 2 | 5.6100 | 5.6100 |  |  |
| 3 | INF (diaphragm) | 0.0383 |  |  |
| 4 | INF | 0.0000 |  |  |
| 5 | INF | 1.3260 | 1.81078 | 40.88 |
| 6 | −0.8084 (aspheric surface) | 0.0000 |  |  |
| 7 | INF | 1.1576 |  |  |
| 8 | INF (image surface) | 0.0000 |  |  |

The basic construction of the imaging optical system of Embodiment 10 is the same as Embodiment 8, and the angle of view is set to 110°, the same as in Embodiment 9. The convex surface of the plano-convex objective lens 18 is an ellipsoidal surface having rotational symmetry about the optical axis, and the eccentricity of the convex surface is −0.6320. The image surface of the object B that is distributed along the surface of the transparent viewing port 16 in the field of view range FV12 is formed so that the depth $\Delta S$ in the direction of the optical axis X of the sagittal image surface is 0.099 mm and the depth $\Delta M$ in the direction of the optical axis X of the meridional image surface is 0.058 mm because the ellipsoidal surface of the objective lens 18 has a larger curvature off-axis than its on-axis curvature, and the amount of deviation from its on-axis curvature increases toward the periphery of the viewing field in the field of view range FV12.

In this case, favorable viewing ability at the periphery of the image can be obtained and focus adjustment can also be easily performed when the position of the image-receiving surface of the solid-state image sensor 23 is arranged with the ability to adjust it in the optical axis direction and directing focusing to the meridional image surface, in this case based on $\Delta M$ being less than $\Delta S$. Furthermore, the technical properties of the objective lens are improved by having a smaller amount of deviation from the on-axis curvature in the field of view range FV12 by setting the aspheric coefficient k to be near the lower limit of the Condition (5) above instead of having a larger on-axis curvature of the ellipsoidal surface in comparison with Embodiment 8. In addition, the thickness of the objective lens at its center on the optical axis is 1.32 mm and the absolute value of the angle of incidence Tw related to the maximum image height position on the image-receiving surface of the image sensor 23 is 15.7° in Embodiment 10.

Generally, it would be expected that each imaging optical system of Embodiments 1 through 10 would be constructed with an optical axis coincident with the optical axis of the objective lens 18 by all the optical structures, including the transparent viewing port, being rotationally symmetric about the optical axis of the objective lens 18. However, even if the center of the viewing port 16 and the optical axis of the objective lens 18 do not coincide, efficiencies of the present invention can be achieved with each of Embodiments 1 through 10 by satisfying Conditions (2) and (4) above. Similarly, an endoscope may be considered to have an optical axis that is the optical axis of the imaging optical system used in the endoscope whether or not the optical axis of the objective lens is precisely coincident with the optical axis of the imaging optical system.

As explained above, the desired imaging characteristics of the present invention relate particularly to the shape of the aspheric surface of the objective lens 18 in each of Embodiments 1 through 10. Therefore, a detailed explanation in regards to the shape of these aspheric surfaces follows. This explanation will make reference to FIGS. 28 through 37 that show graphs of the aspheric displacement, that is, the amount of deviation from a spherical shape of these aspheric surfaces. In each of FIGS. 28 through 37, the aspheric displacement Sag(h) is measured along a line parallel to the optical axis of the objective lens 18 and between a point on a reference spherical surface having the radius of curvature that is equal to the radius of curvature R that the aspheric surface has on the optical axis of the objective lens 18 and a point on the aspheric surface. In particular, the aspheric displacement Sag(h) is given by the following Equation (B):

[Aspheric displacement $Sag(h)$]=−1·[$Sag_a(h)$−$Sag_s(h)$]    Equation (B)

where $Sag_a(h)$ is the coordinate value in the optical axis direction of the point on the aspheric surface at a beam height h; and $Sag_s(h)$ is the coordinate value in the optical axis direction of the point on the spherical surface at the beam height h.

The beam height h is within the range 0<h<IH. In FIGS. 28-37, the left vertical axis is the scale for aspheric displacement Sag(h) and the right vertical axis is the scale for the second derivative of the aspheric displacement Sag(h), which is denoted as Sag"(h).

Figure 29:
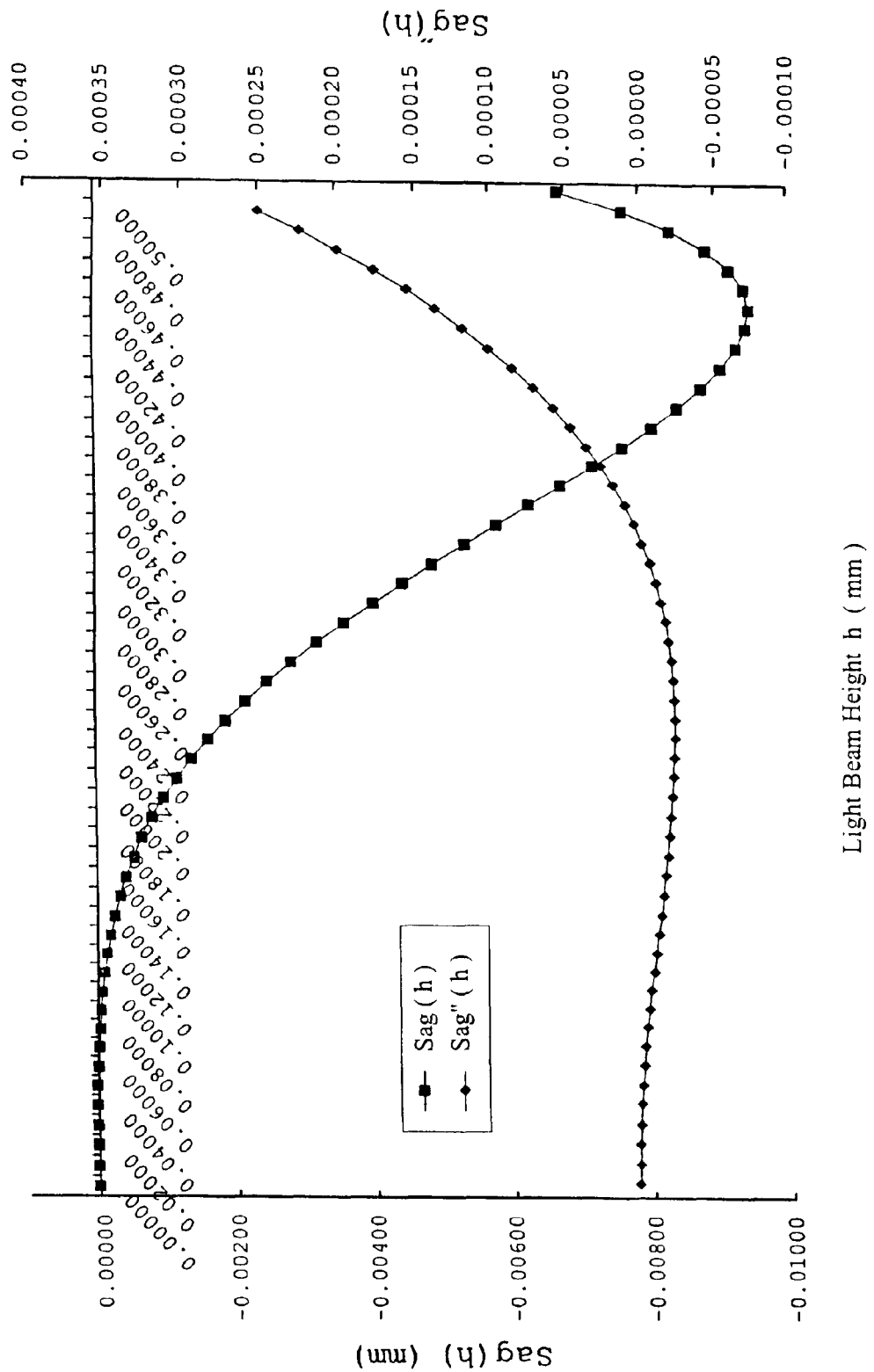
FIG. 29 is a graph showing the aspheric displacement and the second derivative of the aspheric displacement of the aspheric surface of the objective lens of Embodiment 2.
Figure 30:
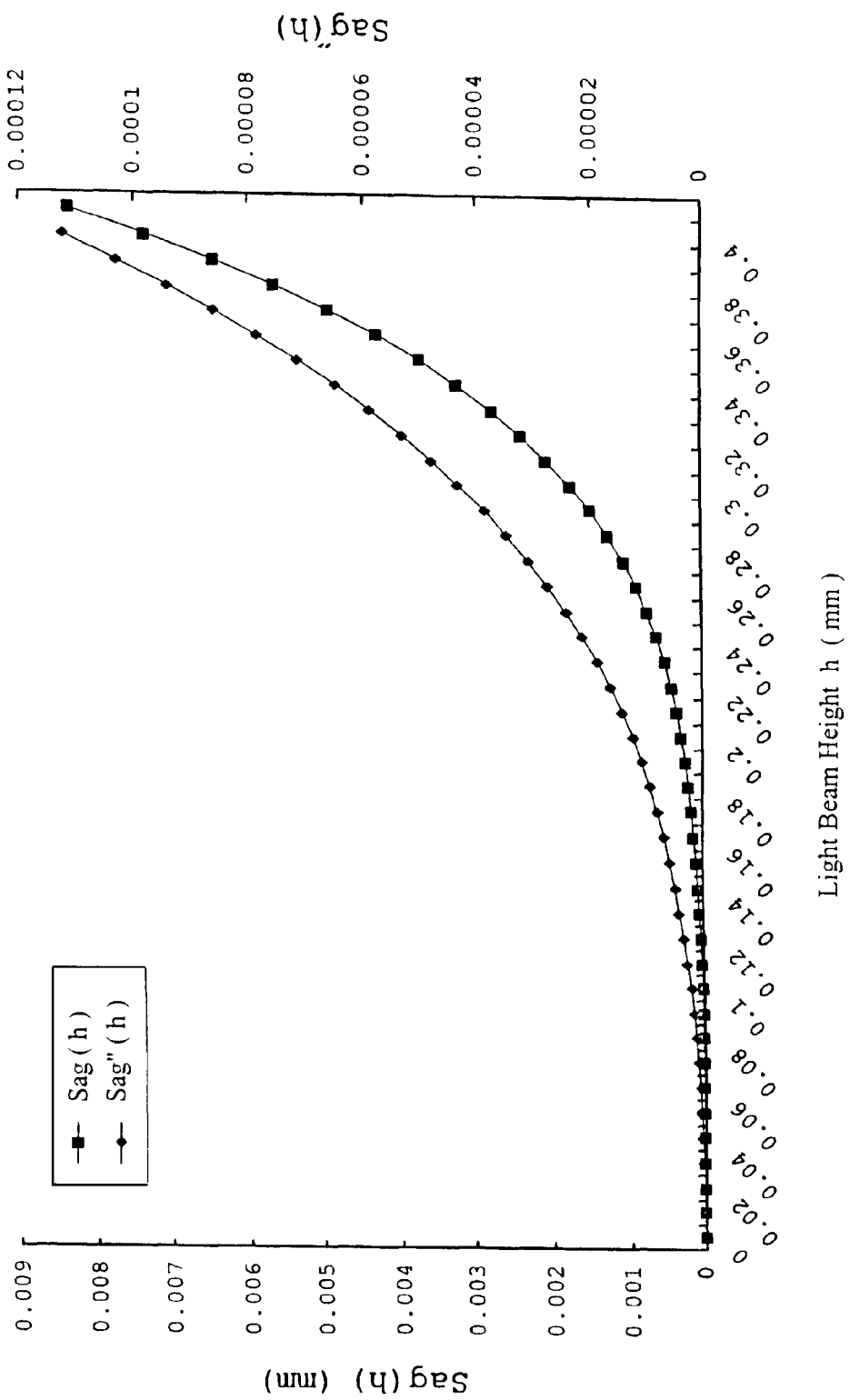
FIG. 30 is a graph showing the aspheric displacement and the second derivative of the aspheric displacement of the aspheric surface of the objective lens of Embodiment 3.
Figure 31:
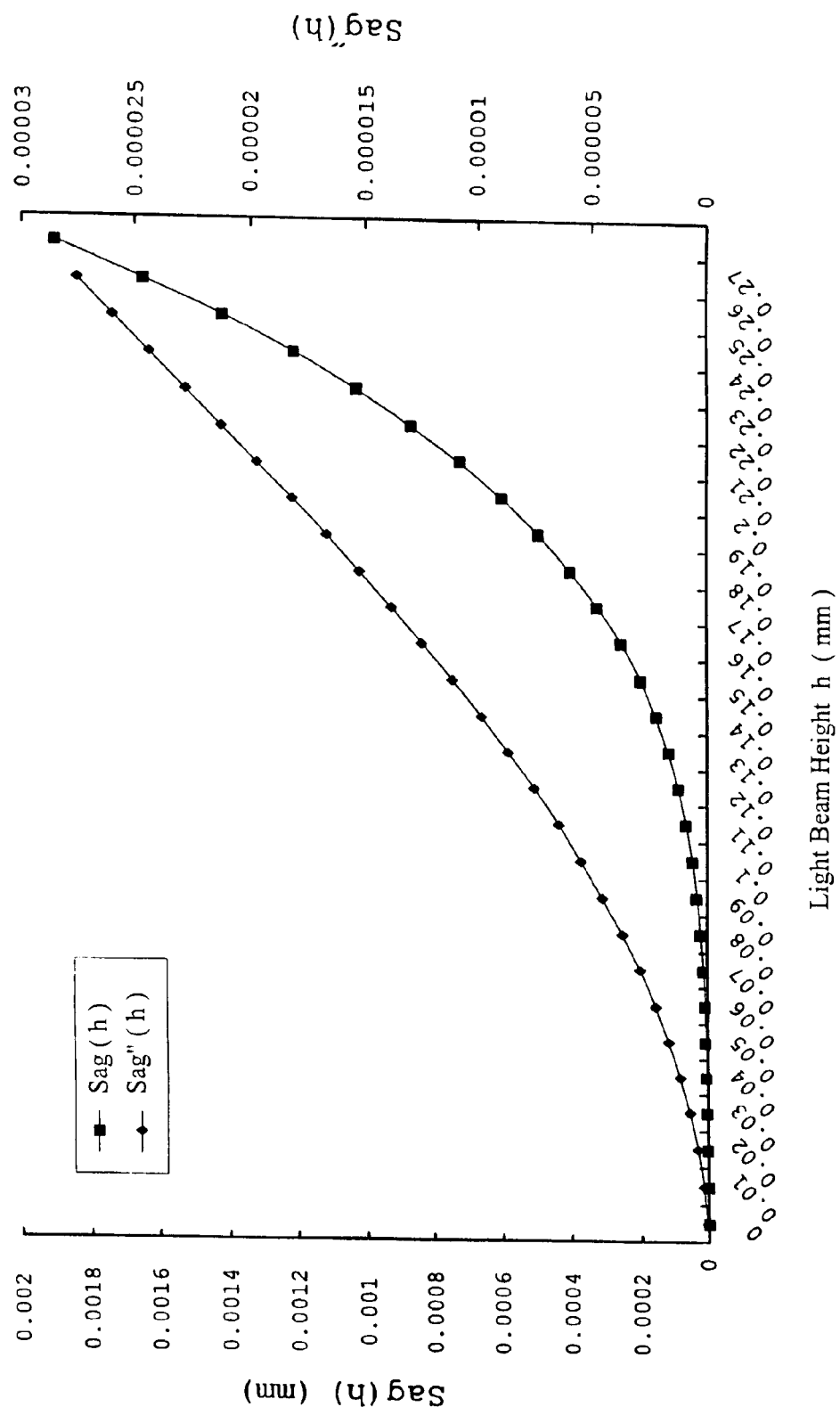
FIG. 31 is a graph showing the aspheric displacement and the second derivative of the aspheric displacement of the aspheric surface of the objective lens of Embodiment 4.
Figure 32:
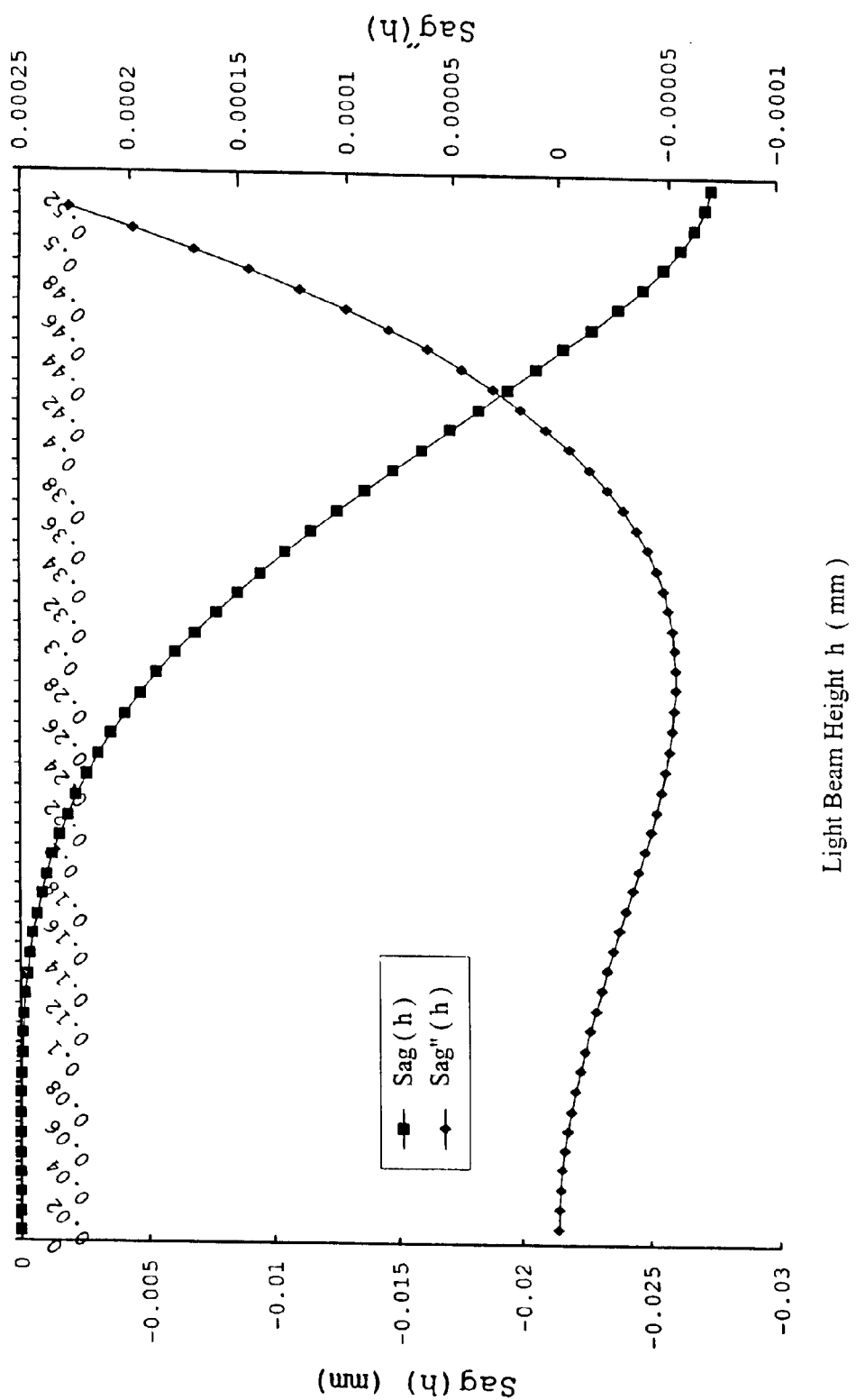
FIG. 32 is a graph showing the aspheric displacement and the second derivative of the aspheric displacement of the aspheric surface of the objective lens of Embodiment 5.
Figure 33:
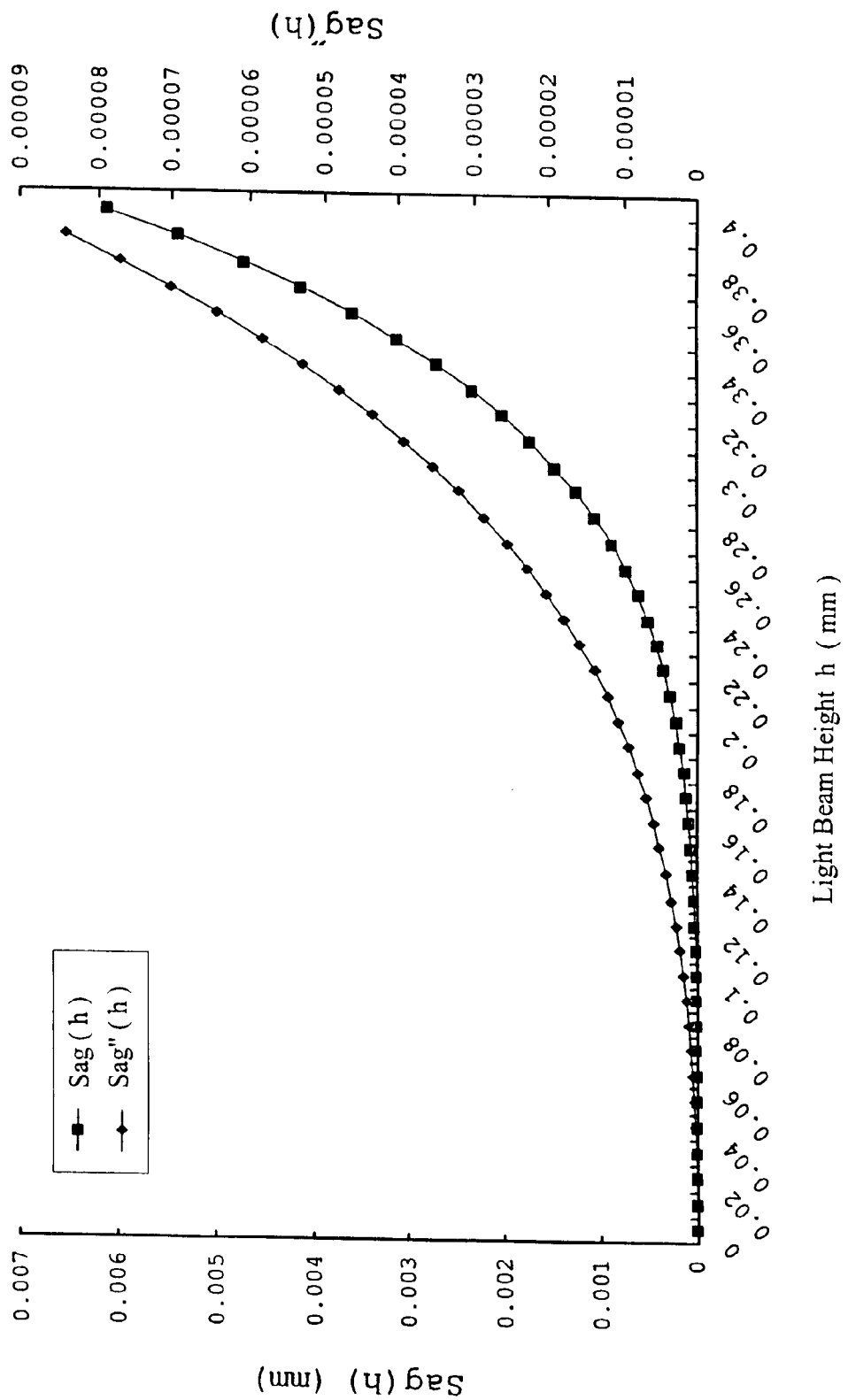
FIG. 33 is a graph showing the aspheric displacement and the second derivative of the aspheric displacement of the aspheric surface of the objective lens of Embodiment 6.
Figure 34:
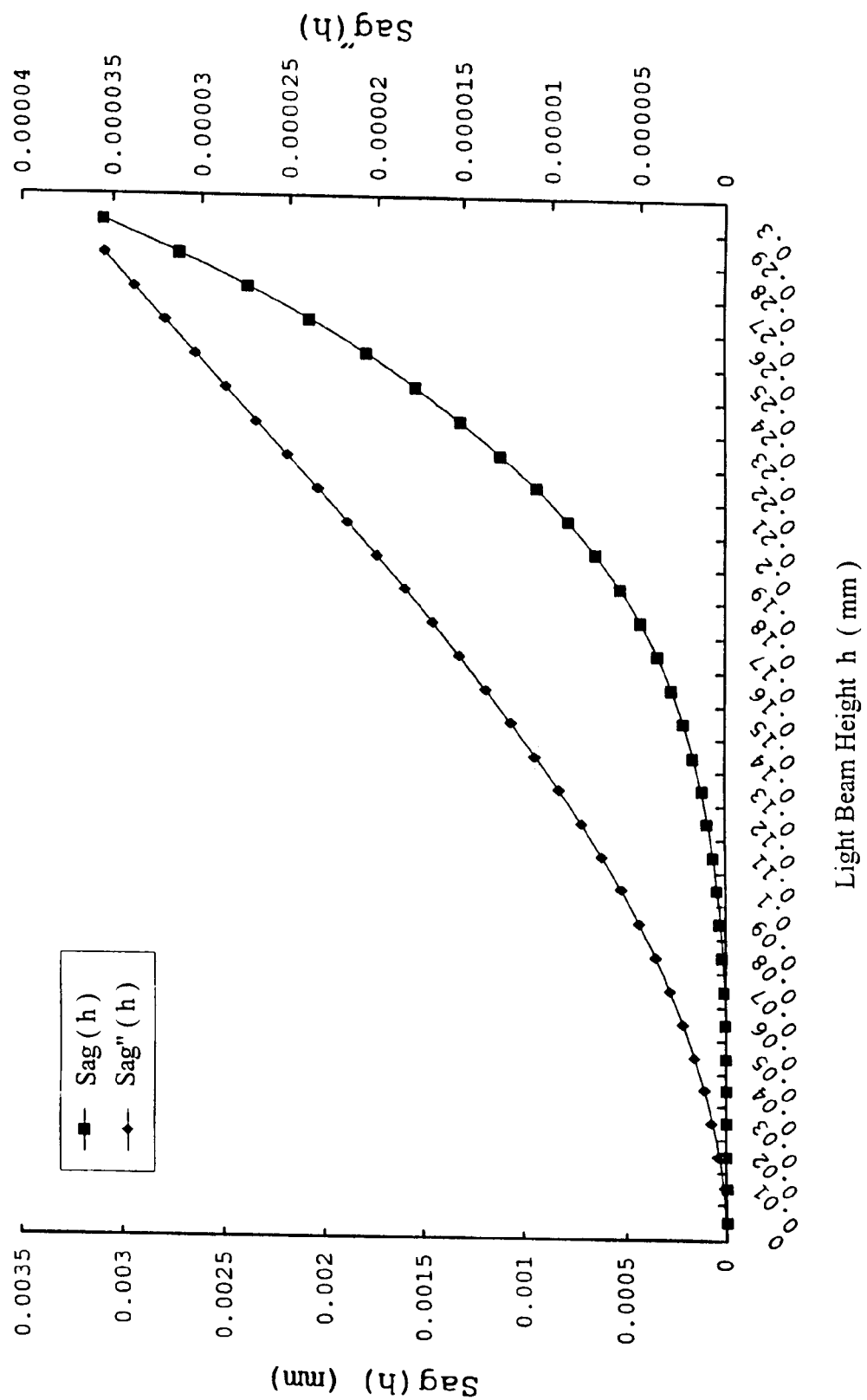
FIG. 34 is a graph showing the aspheric displacement and the second derivative of the aspheric displacement of the aspheric surface of the objective lens of Embodiment 7.
Figure 35:
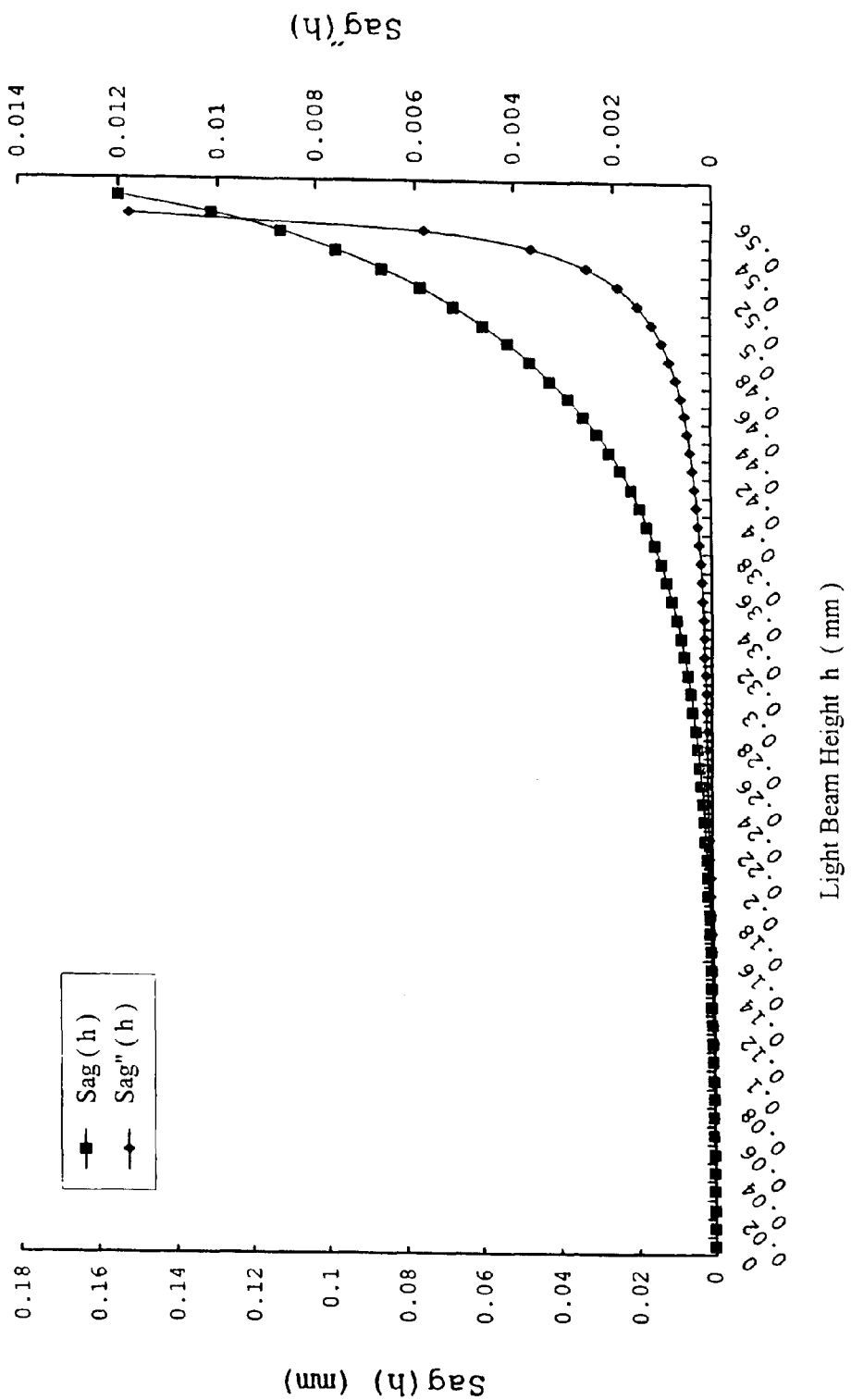
FIG. 35 is a graph showing the aspheric displacement and the second derivative of the aspheric displacement of the aspheric surface of the objective lens of Embodiment 8.
Figure 36:
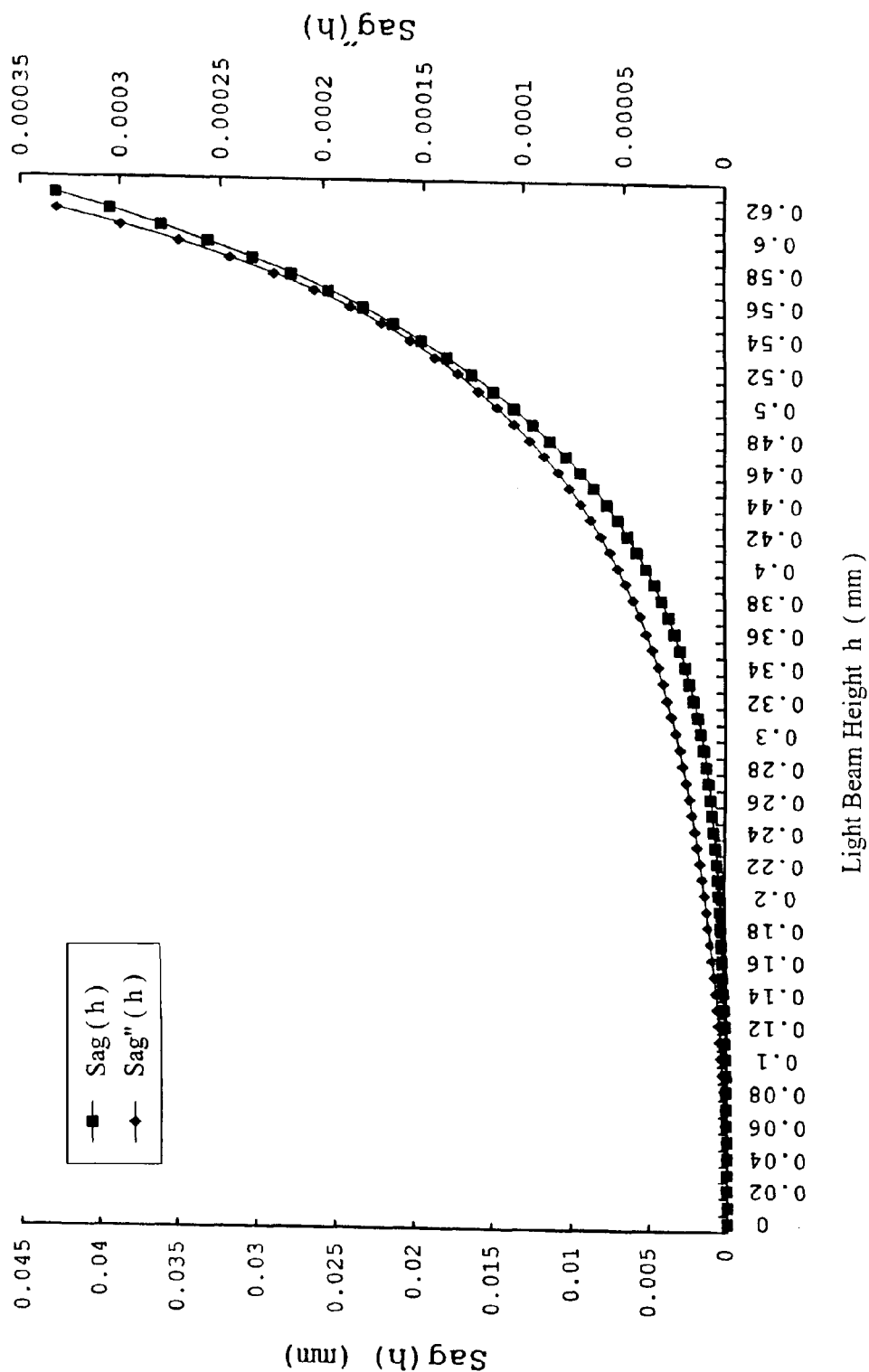
FIG. 36 is a graph showing the aspheric displacement and the second derivative of the aspheric displacement of the aspheric surface of the objective lens of Embodiment 9.
Figure 37:
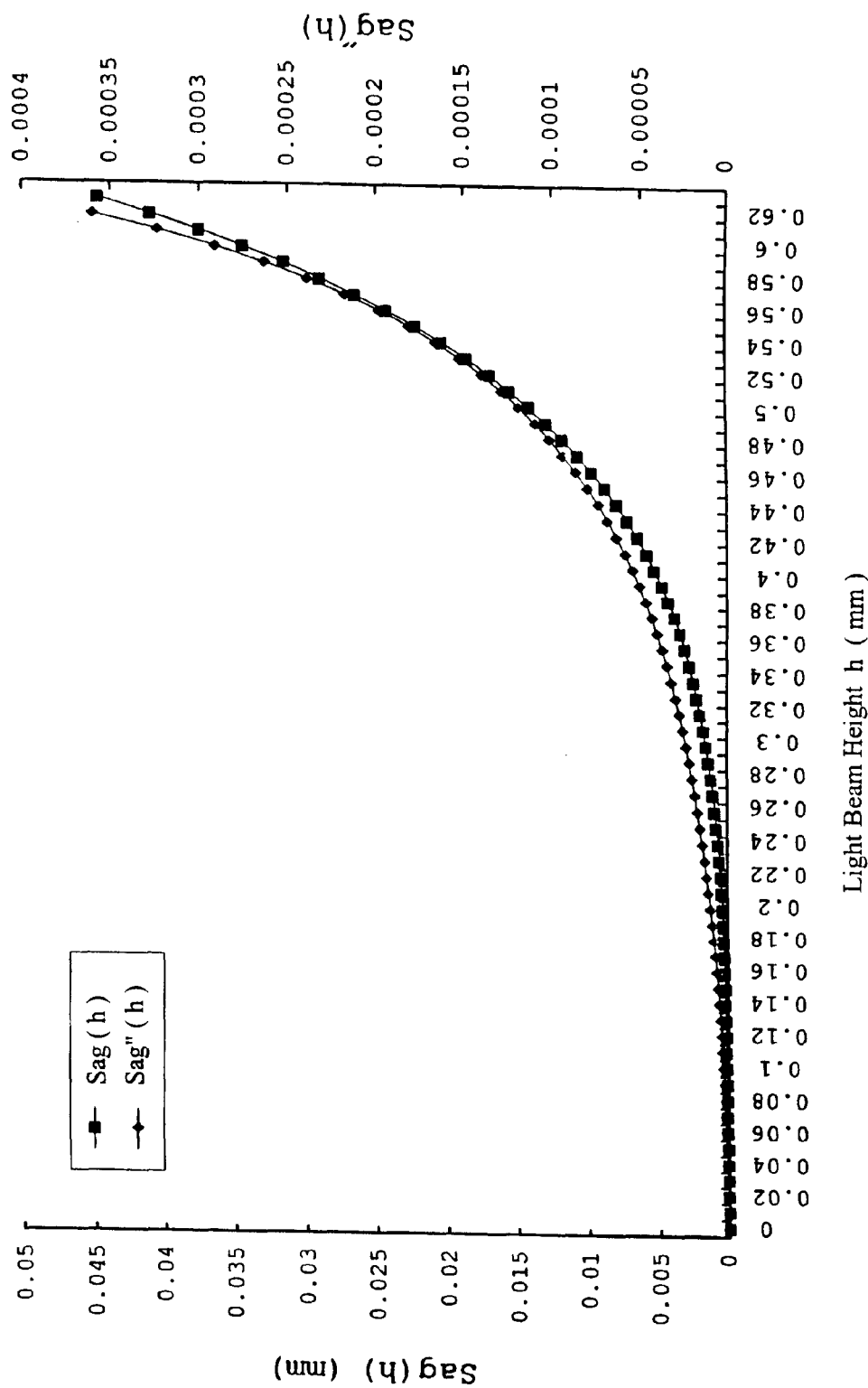
FIG. 37 is a graph showing the aspheric displacement and the second derivative of the aspheric displacement of the aspheric surface of the objective lens of Embodiment 10.

As shown in FIGS. 28-37, the aspheric displacement Sag (h) is positive throughout except in Embodiments 2 and 5 (FIGS. 29 and 32, respectively). In other words, except in Embodiments 2 and 5, the aspheric surfaces have larger curvatures off-axis than the corresponding reference spherical surfaces and serve to correct negative image distortion. When a lens surface has a curved shape similar to the reference spherical surface, it is difficult to minimize distortion in the range of beam height h from IH/2 to IH and it is also difficult to satisfy Condition (4) above. On the other hand, when distortion for a flat surface object is corrected completely, the image surface becomes highly curved, as shown by image surface B in FIG. 1, and the objectives of the present invention cannot be achieved.

Considering the second derivative of the aspheric displacement Sag"(h), FIGS. 28 through 37 show upwardly concave curves for the second derivative, related to correcting negative distortion, as compared to a spherical surface where the second derivative would be a straight line indicating a constant positive second derivative. In the case of Embodiments 2 and 5, although a negative value is included part of the way, the change from a negative to a positive value is shown within the range of the beam height h between IH/2 and IH, with the distance IH being previously defined. This change is along upwardly concave curves, and the operation for correcting negative distortion from a negative to a positive direction is generated within the range of the beam height between IH/2 and IH in this manner. In general, the efficiencies of the present invention can be achieved if there is at least a range of beam heights h where IH/2<h<IH where the following Condition is satisfied:

$-d^2 Sag_a(h)/dh^2 + d^2 Sag_s(h)/dh^2 > 0$    Condition (8)

where $Sag_a(h)$, $Sag_s(h)$, and h are defined as set forth previously.

Furthermore, there is a technique for determining the desired shape of the aspheric surface based on paraxial focal lengths defined in perpendicular directions for curvatures at specific beam heights. Distortion in the sagittal direction and in the meridional direction can be corrected by satisfying the following Condition:

$$0.63 < [fx \cdot (IH)]/[fy \cdot (IH)] < 1 \qquad \text{Condition (9)}$$

where fx is the paraxial focal length in the direction of closer focus related to the curvature at the beam height IH, with the distance IH being as previously defined; and fy is the paraxial focal length in the direction of farther focus related to the curvature at the beam height IH, with the distance IH being as previously defined.

When the quantity fx(IH)/fy(IH) is less than or equal to the lower limit of Condition (9) above, the shape of the aspheric surface approaches that of a spherical surface, making it difficult to minimize distortion in the range of beam heights h from b equals IH/2 to IH. Also, it becomes difficult to satisfy Condition (4) above. Moreover, when the fx(IH)/fy(IH) is equal to one, distortion in relation to a flat object surface is corrected completely, but the distortion for an image surface B as shown in FIG. 1 above becomes excessive.

Furthermore, there is distortion in optical systems generally, and distortion is particularly prominent in optical systems having a wide angle of view, such as endoscopes. However, enlarging the lens diameter for correction is disadvantageous because there is commonly a need to make the optical system as small as possible, and therefore generally distortion is not well corrected. In contrast, however, with an endoscope having a transparent viewing port as in the present invention, it is possible to more easily deal with distortion based on the shapes of the objective lens surfaces and the outer surface of the transparent viewing port. Accordingly, when the object surface shape is defined by being immediately adjacent the surface of the viewing port, a favorable image as to distortion (particularly, in the field of view range FV12) can be obtained when the imaging optical system satisfies the following Condition:

$$-20\% < \Delta D < 26\% \qquad \text{Condition (10)}$$

where $\Delta D$ is the amount of distortion of an image formed by the imaging optical system as determined at the distances IH and IH/2 from the optical axis along straight lines perpendicular to said optical axis, with the distances IH and IH/2 being as previously defined.

When the lower limit of Condition (10) is not satisfied, the image is compressed unnaturally due to barrel distortion becoming large. Furthermore, when the upper limit of Condition (10) is not satisfied, pincushion distortion becomes too large, so that the image expands and appears to be unnaturally stretched.

A method for checking by a simple technique whether or not an imaging optical system satisfies Conditions (2) and (4) above follows. For example, a white and black line pair is placed at the object point position of the transparent viewing port surface that has an image forming relationship with the image at the image position at a distance 4·IH/5 from the center of the effective imaging area of the solid-state image sensor so that the white and black line pair lie in a horizontal direction on the image-receiving surface of the solid-state image sensor, and a corresponding image is displayed on the display surface of a display device. The width of the white and black line pair Ra, in millimeters (mm), that provides ten per cent contrast of the white line and black line is given by the following Equation (C):

$$Ra = 0.028/(\beta local) \qquad \text{Equation (C)}$$

where

Ra, as recited above, is the width (in mm) of the white and black line pair; and $\beta$ local is the magnification of the image position at a distance 4·IH/5 from the center of the effective imaging area of a solid-state image sensor of CIF format.

In each of Embodiments 1-10 described above, an appropriate value of $\beta$ local is approximately 0.24. Using the value 0.24 in Equation (C) above, a value of Ra equal to 0.12 mm is determined. This value represents a threshold value for Conditions (2) and (4) above being satisfied. In other words, when an imaging optical system satisfies the following Condition (11), it will, generally speaking, also satisfy Conditions (2) and (4) above:

$$Ra > 0.12 \text{ mm} \qquad \text{Condition (11)}.$$

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An endoscope including an optical axis, the endoscope comprising:

a spherical or nearly spherical transparent viewing port;

an objective lens that includes at least one aspheric surface and that optically forms an image of an object, said objective lens being formed as a single lens element; and a solid-state image sensor for converting said image into an electronic signal; wherein the following condition is satisfied $$-0.6 < k < -0.85$$

where k is the eccentricity of said aspheric surface; and the shape of said aspheric surface is defined according to the following equation $$X = C \cdot S^2 / [1 + (1 - (k+1) \cdot C^2 \cdot S^2)^{1/2}]$$

where

X is the length of a line segment from a point on said aspheric surface at a distance S from an axis of symmetry of said objective lens as measured perpendicular to said axis of symmetry to the plane that is tangent to the vertex of said aspheric surface; and C=1/R, where R is the radius of curvature of said aspheric surface on said optical axis.

2. The endoscope according to claim 1, wherein:

said solid-state image sensor includes an image-receiving surface for receiving said image, said image-receiving surface being perpendicular to said optical axis and intersecting said optical axis at the center of an effective imaging area of said image-receiving surface; and the following conditions are satisfied:

$$1.51 > D_f/f_L > 0.94$$

$$0° < |Tw| < 16.5°$$

where
- D is the thickness of said objective lens along its axis of symmetry;
- fL is the focal length of the entire imaging optical system; and
- Tw is the angle of incidence of a principal ray of said objective lens on said image-receiving surface at the farthest point from said optical axis when said image is formed on said image-receiving surface.

3. The endoscope according to claim 1, wherein said viewing port, said objective lens, and said image sensor form an imaging optical system, said image is formed along an optical axis of said objective lens, and said image sensor defines an effective imaging area centered on said optical axis, and the following condition is satisfied $$-20\% < \Delta D < 26\%$$

where
- ΔD is the amount of distortion of said image as determined at portions of said image about points of an image surface of said image at distances IH/2 and IH from said optical axis along straight lines perpendicular to said optical axis, and the point at the distance IH is the farthest point from said optical axis within said effective imaging area.

4. The endoscope according to claim 1, wherein said viewing port, said objective lens, and said image sensor form an imaging optical system, said image is formed along an optical axis of said objective lens, and said image sensor defines an effective imaging area centered on said optical axis, and the following condition is also satisfied:

$$w/2 > 50°$$

where
- w is the field angle of said imaging optical system for said effective imaging area.

5. The endoscope according to claim 1, and further including:
- an imaging optical system including an optical axis that includes a spherical or nearly spherical transparent viewing port, an objective lens that includes at least one aspheric surface, is formed as a single lens element, has positive refractive power, and optically forms along said optical axis an image of an object viewed through said transparent viewing port; and
- a display device for displaying an image produced from the image received by said solid-state image sensor;

wherein
said solid-state image sensor includes an image-receiving surface for receiving said image, said image-receiving surface being perpendicular to said optical axis, and said optical axis intersecting said image-receiving surface at the center of an effective imaging area; and the following condition is satisfied:

$$Ra > 0.12 \text{ mm}$$

where
- Ra is the width, in mm, of a white and black line pair having ten percent contrast when said white and black line pair forms said object and said white and black line pair are imaged on said image-receiving surface at a distance 4·IH/5 from said optical axis and IH is the distance of the farthest point from said optical axis within said effective imaging area.

* * * * *